United States Patent
Hernández Míguez et al.

(10) Patent No.: US 9,868,784 B2
(45) Date of Patent: *Jan. 16, 2018

(54) ANTIBODIES AGAINST THE S100P PROTEIN FOR THE TREATMENT AND DIAGNOSIS OF CANCER

(71) Applicant: LYKERA BIOMED SA, Barcelona (ES)

(72) Inventors: José Luis Hernández Míguez, Sant Boi de Llobregat (ES); Jaume Adan Plana, Mataró (ES); Josep Maria Martínez Escolà, Barcelona (ES); Marc Masa Álvarez, Esparreguera (ES); Ramon Messeguer Peypoch, Premiá de Mar (ES); Francesc Mitjans Prat, Igualada (ES); Sheila Dakhel Plaza, Esparreguera (ES); Antonio Coll Manzano, Barcelona (ES); Rosa M$^a$ Hervas Villegas, L'Hospitalet de Llobregat (ES); Carme Calvis Calpe, L'Hospitalet de Llobregat (ES); Laura Padilla García, Segur de Calafell (ES); Lourdes Tatiana Roque Navarro, Barcelona (ES); Laura Barberà Ferrando, Jesus-Tortosa (ES); Manuel Rivas Cañas, Sant Boi de Llobregat (ES)

(73) Assignee: LYKERA BIOMED SA, Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 14/961,106

(22) Filed: Dec. 7, 2015

(65) Prior Publication Data

US 2016/0090412 A1 Mar. 31, 2016

Related U.S. Application Data

(62) Division of application No. 13/985,121, filed as application No. PCT/EP2012/050653 on Jan. 17, 2012, now Pat. No. 9,228,011.

(30) Foreign Application Priority Data

Jan. 17, 2011 (EP) .................................... 11382010

(51) Int. Cl.
| | | |
|---|---|---|
| A61K 39/395 | (2006.01) | |
| C07K 16/18 | (2006.01) | |
| C07K 14/47 | (2006.01) | |
| C07K 16/24 | (2006.01) | |
| C12R 1/91 | (2006.01) | |
| A61K 31/704 | (2006.01) | |
| G01N 33/574 | (2006.01) | |
| A61K 45/06 | (2006.01) | |
| A61K 39/00 | (2006.01) | |

(52) U.S. Cl.
CPC ............ *C07K 16/18* (2013.01); *A61K 31/704* (2013.01); *A61K 39/3955* (2013.01); *A61K 39/39558* (2013.01); *A61K 45/06* (2013.01); *C07K 14/4728* (2013.01); *C07K 16/24* (2013.01); *C12R 1/91* (2013.01); *G01N 33/57438* (2013.01); *G01N 33/57488* (2013.01); *A61K 2039/505* (2013.01); *C07K 2317/14* (2013.01); *C07K 2317/33* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,849,528 A | 12/1998 | Hillman et al. | |
| 9,228,011 B2 * | 1/2016 | Hernandez Miguez | ............. A61K 39/3955 |
| 2003/0096337 A1 | 5/2003 | Hillman et al. | |
| 2005/0009067 A1 | 1/2005 | Logsdon et al. | |
| 2006/0053498 A1 | 3/2006 | Bejanin et al. | |
| 2008/0064113 A1 | 3/2008 | Goix et al. | |
| 2010/0068736 A1 | 3/2010 | Pollock et al. | |
| 2014/0030823 A1 | 1/2014 | Sanuki et al. | |

FOREIGN PATENT DOCUMENTS

| | | |
|---|---|---|
| JP | 2007224009 | 9/2007 |
| WO | WO 01/22920 | 4/2001 |
| WO | WO 03/101283 | 12/2003 |
| WO | WO 2004/081573 | 9/2004 |
| WO | WO 2004/092338 | 10/2004 |

(Continued)

OTHER PUBLICATIONS

Strome et al., The Oncologist, 2007; 12:1084-95.*
Brand et al., Anticancer Res. 2006; 26:463-70.*
Kataja et al., Ann Oncol 2009; 20(sup 4): iv10-14.*
Nelson et al., Ann. Intern Med. 2009; 151:727-737.*
Balmana et al. Ann Oncol 2009; 20(supp 4):iv19-20.*
Barry S,. Cmogorae-Jureevic T. 2009. S1OOP (S 100 calcium binding protein o), . . . Atlas Genet Cytogenet Oneol Haematol,. vol. 13 n° 6.

(Continued)

*Primary Examiner* — Sheela J. Huff
(74) *Attorney, Agent, or Firm* — Greer, Burns & Crain, Ltd.

(57) ABSTRACT

The present invention relates to the use of antibodies against the S100P protein for the prevention and/or treatment of cancer; and to methods and kits for diagnosing cancer in vitro by means of detecting the levels of S100P in a biofluid, preferably with an antibody. The invention also relates to specific anti-S100P monoclonal antibodies, hybridoma cell lines producing them and method for obtaining them, as well as to pharmaceutical compositions and conjugates containing them.

5 Claims, 6 Drawing Sheets

(56) References Cited

FOREIGN PATENT DOCUMENTS

| WO | WO 2008/154638 | 12/2008 |
| WO | WO 2010/047448 | 4/2010 |

OTHER PUBLICATIONS

Nakata K. et al. 2010. Human Pathology, 41 (6): 824-831.
Ohuchida K. et al. 2006. Clinical Cancer Research, 12(18): 5411-5416.
Parkkila S. et al. 2008. BMC Clinical Pathology, 8(1): 2.
Arumugam, T. et al. 2005. Clinical Cancer Research, 11(15): 5356-5364.
Arumugam, T. et al. 2006. Journal of the National Cancer Institute, 98(24): 1806-1818.
Arumugam, T. et al. 2010. Amino acids; The Forum for Amino Acid and Protein Research, 41(4): 893-899.
Levy M. et al. 2010. Human Pathology, 41 (9): 1210-1219.
Anandan V. et al. 2010. Laboratory Investigation, 90(1): 87A.
Hamada, S. et al. 2010. Cancer Science, 102(1): 150-156.
Brown et al (J. Immunol. May 1996; 156(9):3285-3291).
Vajdos et al (J. Mol. Biol. Jul. 5, 2002;320(2); 415-428).

* cited by examiner

ANTIBODIES AGAINST THE S100P PROTEIN FOR THE TREATMENT AND DIAGNOSIS OF CANCER

CROSS-REFERENCE TO RELATED APPLICATIONS

This application is a divisional application of U.S. patent application Ser. No. 13/985,121, filed on Oct. 14, 2013, which is a 371 filing of PCT/EP2012/050653 filed on Jan. 17, 2012, which claims the benefit of priority from European Patent Application EP 11382010.4 filed on Jan. 17, 2011, the entire disclosures of which are incorporated herein by reference.

TECHNICAL FIELD OF THE INVENTION

The present invention relates to the use of antibodies against the S100P protein for the prevention and/or treatment of cancer; and to methods and kits for diagnosing cancer in vitro by means of detecting the levels of S100P in a biofluid, preferably with an antibody. The invention also relates to specific anti-S100P monoclonal antibodies, hybridoma cell lines producing them and method for obtaining them, as well as to pharmaceutical compositions and conjugates containing them.

BACKGROUND OF THE INVENTION

The S100P protein is a member of the family of calcium binding proteins called S100 (Zhang H. et al. 2003. J Mol Biol, 325:785-794) which presents high expression levels in a wide variety of different tumor types. Encompassing all of tumor development, its activity is mainly associated with the establishment of tumor cell resistance to chemotherapy treatments (Bertram J. et al. 1998. Anticancer Drugs, 9:311-317), an increase of the proliferative and invasive capacity for the tumor cell and a greater metastatic capacity. Accordingly, there is a correlation between high expression levels of S100P in a tumor and a low life expectancy in patients with cancer.

The gene encoding the S100P protein is expressed in several forms of the disease, including pancreatic cancer (Logsdon C. D. et al. 2003. Cancer Res, 63:2649-2657), breast cancer (Guerreiro Da Silva I. D. et al. 2000. Int J Oncol, 16:231-240; Wang G. et al. 2006. Cancer Res, 66:1199-1207), colon cancer (Fuentes M. K. et al. 2007. Dis Colon Rectum, 50:1230-1240), prostate cancer (Mousses S. et al. 2002. Cancer Res, 62:1256-1260), lung cancer (Diederichs S. et al. 2004. Cancer Res, 64:5564-5569) and ovarian cancer (Surowiak P. et al. 2007. Histopathology, 51:125-128), among others. The S100P protein has intra- and extracellular function and, specifically, at the extracellular level, secreted by the tumor cell, it is known to have an autocrine interaction with the RAGE receptor present in the tumor cell membrane, activating the aforementioned mechanism (Arumugam T. et al. 2004. J Biol Chem, 279:5059-5065).

Several studies have confirmed the benefits of blocking S100P/RAGE in tumor cells by developing peptide antagonists of S100P and small molecules such as cromolyn (Arumugam T. and Logsdon C. D. 2010. Amino acids).

Therefore, there is a need in the state of the art to provide new therapeutic approaches for the treatment of cancer targeting the S100P protein.

In addition, at a diagnostic level, S100P can be considered a good marker in the differentiation process of a normal cell towards a tumor cell, and therefore it is a good biomarker in the cytological examination of tumors. In this regard, anti-S100P monoclonal antibodies potentially useful for the immunohistochemical detection of the expression of S100P in cancerous tissue are known (Parkkila S. et al. 2008. BMC Clinical Pathology, 8:2). This type of analysis presents the drawback of requiring a patient biopsy. Therefore, there is a need in the state of the art to provide a simpler and less invasive method for the clinical diagnosis of cancer by means of detecting the levels of S100P in a subject.

SUMMARY OF THE INVENTION

In a first aspect, the invention relates to the use of an antibody which binds specifically to the S100P protein or of a fragment thereof with capacity for binding to the antigen for the preparation of a medicament for the prevention and/or treatment of cancer.

In another aspect, the invention relates to a specific anti-S100P monoclonal antibody produced by a hybridoma selected from the group of ECACC 10121601, ECACC 10121602, ECACC 10121603 and ECACC 10121604 wherein the hybridomas were deposited with the Health Protection Agency Porton Down and European Collection of Cell Cultures in Porton Down, Salisbury, SP4 OJG, United Kingdom on Dec. 16, 2010; or a polypeptide having at least one fragment of the sequence of said monoclonal antibody with capacity for binding to S100P.

In another aspect, the invention relates to a hybridoma cell line selected from those cell lines deposited with accession number ECACC 10121601, ECACC 10121602, ECACC 10121603 and ECACC 10121604.

In additional aspects, the invention relates to a conjugate comprising a monoclonal antibody produced by a hybridoma selected from the group of ECACC 10121601, ECACC 10121602, ECACC 10121603 and ECACC 10121604 or a polypeptide having at least one fragment of the sequence of said monoclonal antibody, and a second component selected from the group of:

(a) a cytotoxic agent
(b) an antiangiogenic agent
(c) an antimetastatic agent as well as to the uses thereof for the preparation of a medicament for the prevention and/or treatment of cancer.

In yet another aspect, the invention relates to a method for obtaining a monoclonal antibody of the invention which comprises culturing a hybridoma cell line selected from those cell lines deposited with accession number ECACC 10121601, ECACC 10121602, ECACC 10121603 and ECACC 10121604 in conditions which allow the production of said antibody.

In another aspect, the invention relates to a pharmaceutical composition comprising a pharmaceutically effective amount of at least one monoclonal antibody produced by a hybridoma selected from the group of ECACC 10121601, ECACC 10121602, ECACC 10121603 and ECACC 10121604 or a polypeptide having at least one fragment of the sequence of said monoclonal antibody with capacity for binding to S100P and at least one pharmaceutically acceptable excipient. In another aspect, the invention relates to an in vitro method for diagnosing cancer in a subject which comprises:

(a) detecting the levels of the S100P protein or of a variant thereof in a biofluid of said subject (b) comparing said levels with a reference value wherein increased levels of the S100P protein or of a variant thereof with respect to the reference value are indicative of the subject suffering from cancer.

In another aspect, the invention relates to a kit for diagnosing cancer in a biofluid which comprises at least one specific anti-S100P monoclonal antibody produced by a hybridoma selected from the group of ECACC 10121601, ECACC 10121602, ECACC 10121603 and ECACC 10121604 or a polypeptide having at least one fragment of the sequence of said monoclonal antibody with capacity for binding to S100P.

In another aspect, the invention relates to a composition comprising, together or separated, an antibody that binds specifically to the S100P protein or of a fragment thereof with capacity for binding to the antigen and a chemotherapeutic agent.

In a further aspect, the invention relates to an antibody that binds specifically to the S100P protein or a fragment thereof with capacity for binding to the antigen for use in the prevention and/or treatment of cancer.

DETAILED DESCRIPTION OF THE INVENTION

Figure 1:
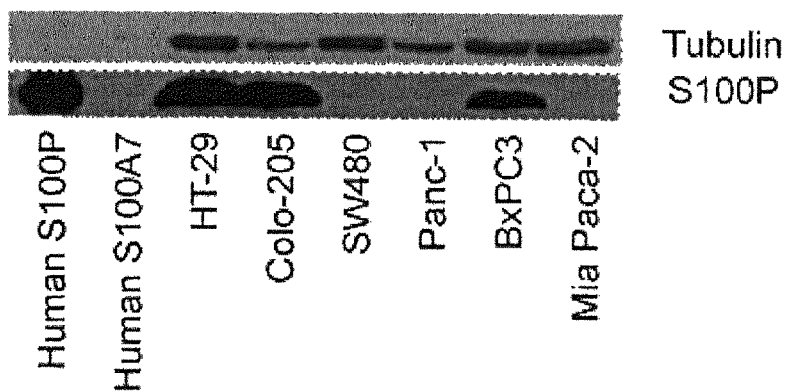
FIG. 1 (panels A and B) shows the expression levels of S100P in total protein extracts of tumor cells of different origins and of the primary culture of HUVEC, determined by Western-blot and checking the specificity of the 3F8 monoclonal antibody of the invention. Three breast adenocarcinoma tumor lines (MDA-MB-231, MDA-MB-468 and MCF7 as shown in FIG. 1, panel B), three pancreatic adenocarcinoma tumor lines (MiaPaca-2, Panc-1 and BxPC3 as shown in FIG. 1, panel A), three colon adenocarcinoma tumor lines (Colo205, HT29 and SW480 as shown in FIG. 1, panel A), a prostate adenocarcinoma tumor line (PC3 as shown in FIG. 1, panel B), another ovarian adenocarcinoma tumor line (OVCAR-3 as shown in FIG. 1, panel B) and a primary culture of human umbilical vein endothelial cells (HUVEC as shown in FIG. 1, panel B) were used. Samples of the human recombinant proteins S100P (positive control) and S100A7 (negative control) were also analyzed.
Figure 1:
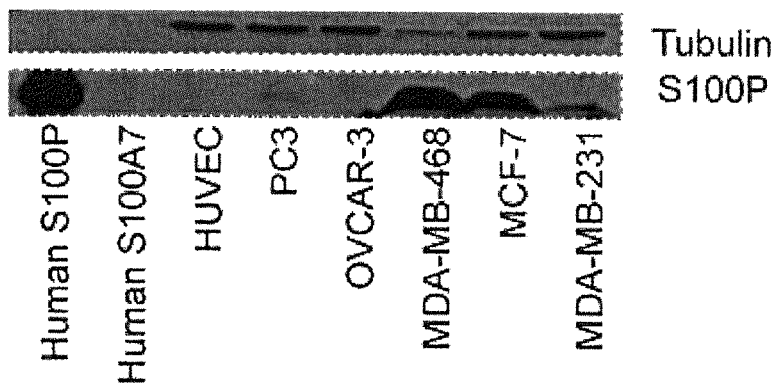

The authors of the present invention have surprisingly discovered that monoclonal antibodies directed against the S100P protein are capable of neutralizing the proliferative capacity induced by S100P in a functional in vitro tumor proliferation assay. These results indicate that the anti-S100P antibodies are useful for the prevention and/or treatment of cancer. The authors of the present invention have also found that monoclonal antibodies directed against the S100P protein have antimetastatic activity.

The authors of the present invention have additionally demonstrated that the levels of S100P in a biofluid are suitable as a diagnostic marker for the early detection of cancer. Therefore, the present invention also relates to an in vitro method and to kits for the diagnosis of cancer in a patient by means of detecting the levels of S100P in a biofluid, especially with antibodies.

Therapeutic Uses of the Anti-S100P Antibodies

The anti-S100P antibodies capable of binding specifically to the S100P protein have an application in those diseases in which said protein is overexpressed.

Specifically, the S100P protein is expressed, as has been described above, in a wide variety of cancers.

As a result, the S100P protein ligands, and more specifically, antibodies specific against this protein, are candidate drugs to be used in therapy for the treatment of said disease.

Thus, in one aspect, the invention relates to the use of an antibody which binds specifically to the S100P protein or of a fragment thereof with capacity for binding to the antigen for the preparation of a medicament for the prevention and/or treatment of cancer.

In another aspect, the invention relates to an antibody which binds specifically to the S100P protein or a fragment thereof with capacity for binding to the antigen for its use in the preparation of a medicament for the prevention and/or treatment of cancer.

In another aspect, the invention relates to a method of treatment or prevention of cancer in a subject which comprises the administration to said subject of an antibody which binds specifically to the S100P protein or of a fragment thereof with capacity for binding to the antigen.

As it is used in the present invention, the term "antibody" relates to a monomeric or multimeric protein which comprises at least one polypeptide having the capacity for binding to a determined antigen and comprising all or part of the light or heavy chain variable region of an immunoglobulin molecule. The term antibody includes any type of known antibody, such as, for example, polyclonal antibodies, monoclonal antibodies and genetically engineered antibodies, such as chimeric antibodies, humanized antibodies, primatized antibodies, human antibodies and bispecific antibodies.

The basic structural unit of a typical antibody is a tetramer, which is made up of two identical pairs of polypeptide chains, each pair having a "light" or L chain (approximately 25 kDa) and a "heavy" or H chain (approximately 50-70 kDa). The amino-terminus part of each chain includes a variable region of approximately 100 to 110 or more amino acids which are mainly responsible for antigen recognition; whereas the carboxyl-terminus part of each chain defines a constant region, mainly responsible for the effector function. The light chains consist of a variable region (VL) and a constant region (CL); whereas the heavy chains have a variable region (VH) and three constant regions (CH1, CH2, CH3). Within the light and heavy chains, the variable and constant regions are bound together by means of a "J" region of approximately 12 or more amino acids, the heavy chain also including a "D" region of approximately 10 more amino acids. In general, see Fundamental Immunology Cap. 7 (Paul, W., ed., $2^{nd}$ ed. Raven Press, N.Y. (1989)). The variable regions of each pair of light/heavy chains form the antibody binding site, such that an intact antibody typically has two equal binding sites.

All the chains have the same general structure of relatively conserved framework regions (FR) bound by means of three hypervariable regions, also referred to as complementarity determining regions or CDRs. The CDRs of the two chains of each pair are aligned by means of the framework regions, and the CDR regions are responsible for binding to a specific epitope. From the N-terminus end to the C-terminus end, both the light and heavy chains comprise the FR1, CDR1, FR2, CDR2, FR3, CDR3 and FR4 domains. The assignment of amino acids to each domain is according to the definitions of the Kabat sequences of proteins of immunological interest (National Institutes of Health, Bethesda, Md. (1987 and 1991); Chothia and Lesk J. Mol. Biol. 196:901-917 (1987); Chothia et al. Nature 342:878-883 (1989)).

In the present invention, "polyclonal antibodies" are understood as antibodies derived from different B-cell lines, i.e., antibodies which are a mixture of immunoglobulins, secreted against a specific antigen (S100P), each of which recognizes different epitopes.

"Monoclonal antibodies" are understood as identical homogenous antibodies produced by a hybrid cell product of the fusion of a B-cell clone descendent of a single unique parent cell and a tumor plasma cell. In a particular embodiment, the antibody is a monoclonal antibody.

"Chimeric antibodies" are understood as antibodies constructed with variable regions of an antibody of a species (usually a mammal in which the monoclonal antibody was generated) and constant regions of another species (that species in which the chimeric antibody is going to be used). The objective of said construct is to obtain an antibody with the original monoclonal antibody but which is less immunogenic and better tolerated in the subject who is going to be treated, with an improved serum half-life and which can be recognized by immunological effector mechanisms, i.e., the complement, the Fc receptor of cytotoxic cells or other specific immunoglobulin receptors which show species specificity. In a preferred embodiment, the chimeric antibodies are formed by murine variable regions and human constant regions.

"Humanized antibody" is understood as an antibody from a nonhuman antibody, typically a murine antibody, which conserves the antigen binding properties of the parent antibody, but which is less immunogenic in human beings. This can be achieved by means of different processes, which include (a) grafting the complete nonhuman variable domains into human constant regions to generate chimeric antibodies; (b) grating only the nonhuman complementarity determining regions (CDR) in a human framework and the constant regions, with or without retaining the critical framework residues; and (c) transplanting the complete nonhuman variable domains, but "concealing them" with a section similar to the human variable domain by means of replacing the surface residues.

"Primatized antibody" is understood as a recombinant antibody that has been genetically manipulated to contain the heavy and light variable domains of a monkey antibody (or of another primate), particularly an antibody of a cynomolgus monkey, and containing sequences of a human constant domain, preferably the constant domain of human gamma 1 or 4 immunoglobulin (or a PE variant). The preparation of said antibodies is described in Newman et al., Biotechnology, 10: 1458-1460 (1992); and in patent documents U.S. Pat. No. 5,658,570 and U.S. Pat. No. 6,113,898. It has been described that these antibodies show a high degree of homology with human antibodies, i.e., 85-98%, they have human effector functions, they have lower immunogenicity and can show a high affinity for human antigens. Another very effective means for generating recombinant antibodies is described by Newman, Biotechnology, 10: 1455-1460 (1992).

"Human antibody" is understood as an antibody integrally containing human light and heavy chains as well as constant regions, produced by means of any of the known standard methods.

"Bispecific antibodies" or "bifunctional antibodies" are understood as antibodies having binding specificities for at least two different epitopes. The exemplary bispecific antibodies can bind to two different epitopes of the B-cell surface marker. Others of the said antibodies can bind to a first B-cell marker and additionally bind to a second B-cell surface marker. Alternatively, a binding arm of an anti-B cell marker can be combined with an arm which binds to a triggering molecule in a leukocyte, such as a T-cell receptor molecule (for example, CD2 or CD3), or Fc receptors for IgG (FcγR), such as FcγRI (CD64), FcγRII (CD32) and FcγRIII (CD 16), such that the mechanisms of cell defense are concentrated in the B-cell. Bispecific antibodies can also be used to locate cytotoxic agents against the B-cell. These antibodies have a binding arm to the marker of the lymphocyte and an arm which binds to the cytotoxic agent (for example, saporin, anti-interferon-α, vinca alkaloid, ricin A-chain, methotrexate or a radioactive hapten isotope). Bispecific antibodies can be prepared as whole antibodies or as antibody fragments (for example, F(ab)₂ bispecific antibodies).

The invention also comprises the use of fragments of the different types of antibodies mentioned above. The term "antibody fragment" includes antibody fragments such as Fab, F(ab')₂, Fab', single chain Fv fragments (scFv), diabodies and nanobodies.

Papain digestion of antibodies produces two identical antigen binding fragments referred to as "Fab" fragments, each with a single antigen binding site, and a residual "Fc" fragment, the name of which reflects its capacity for readily crystallizing. Pepsin treatment yields an F(ab')2 fragment which has two antigen binding sites and which is still capable of cross-linking to the antigen.

"Fv" is the minimal antibody fragment containing a complete antigen binding and antigen recognition site. This region consists of a variable domain of a variable light chain and heavy chain dimer in a strong noncovalent association. In this configuration the three hypervariable regions of each variable domain interact to define an antigen binding site on the surface of the VH-VL dimer. As a whole, the six hypervariable regions confer antigen-antibody specificity to the antibody. However, even a single variable domain (or half an Fv, which comprises only three hypervariable regions specific for an antigen) has antigen recognition and binding capacity, although with less affinity than the complete binding site.

The Fab fragment also contains the constant domain of the light chain and the first constant domain (CH1) of the heavy chain. Fab' fragments differ from Fab fragments in the addition of a few residues at the carboxy terminus of the domain CH1 of the heavy chain, including one or more cysteines of the antibody hinge region.

The "single chain Fv" or "scFv" antibody fragments comprise the VH and VL domains of an antibody, in which these domains are present in a single polypeptide chain. Preferably, the Fv polypeptide additionally comprises a linker polypeptide between the VH and VL domains which allows the scFv to form the desired structure for antigen binding. For a review of scFv, see Pluckthun in The Pharmacology of Monoclonal Antibodies, vol. 113, Rosenburg and Moore eds., Springer-Verlag, N.Y., pp. 269-315 (1994).

The term "diabodies" refers to small antibody fragments with two antigen binding sites, those fragments comprising a heavy chain variable domain (VH) connected to a light chain variable domain (VL) in the same polypeptide chain (VH-VL). By means of using a linker which is too short to allow pairing between the two domains in the same chain, the domains are forced to pair with the complementary domains of another chain and create two antigen binding sites. Diabodies are described in further detail in, for example, documents EP 404,097; WO 93/11161; and Hollinger et al., Proc. Natl. Acad. Sci. USA, 90: 6444-6448 (1993).

The term "nanobodies" designates small sized entities (15 kDa) formed solely by the antigen binding region of the heavy chain (VH fragment) of immunoglobulins. Said nanobodies are mainly produced after immunizing animals of the Camelidae family, such as camels, llamas and dromedaries, mainly llamas; and also of the shark family, which have the particularity of having antibodies which naturally lack the light chain and recognize the antigen by the heavy chain variable domain. Nevertheless, the nanobodies derived from these sources require a humanization process for their therapeutic application. Another potential source for obtaining nanobodies is from antibodies derived from different human samples by separating the VH and VL domains of the variable region. Nanobodies present advantages such as a production cost reduction with respect to whole antibodies, stability and the reduction of immunogenicity.

The antibody fragments included in the present invention conserve the capacity for binding to the S100P antigen of the whole antibody they come from, and they also conserve the function of inhibiting one or more characteristic functions of the S100P protein, such as binding activity, signaling activity and/or the stimulation of a cell response. For example, in one embodiment, an antibody fragment can inhibit the interaction of the S100P protein with one or more of its ligands, especially with its RAGE ligand, and/or it can inhibit one or more functions mediated by said protein, such as the tumor cell proliferation.

The antibodies useful in the invention must bind specifically to the S100P protein. As it is used herein, the expression "binds specifically to" refers to the capacity of the antibodies for binding specifically to the S100P protein and not to other proteins of the S100 family.

To identify the antibodies with the desired specificity, immunochemical assays, such as immunofluorescence, flow cytometry, Western blot and ELISA assays, radioimmunoassays, immunohistochemical assays, immunoprecipitations or other immunochemical assays known in the art, can be used. A number of protocols for competitive binding or immunoradiometric assays are known in the state of the art. Said immunoassays typically involve measuring the formation of a complex between an antibody and an immunogen of the S100P protein.

As it is used herein, the term "S100P" refers to a protein belonging to the family of calcium binding proteins called S100, which is overexpressed in tumor cells and associated with tumor proliferation, the invasive and metastatic capacity of tumor cells and with the resistance to chemotherapy. The term also includes all the physiologically relevant post-translational chemical modifications forms, for example, glycosylation, phosphorylation or acetylation, etc., provided that the functionality of the protein is maintained. Said term encompasses the S100P of any mammal species, including but not being limited to domestic and farm animals (cows, horses, pigs, sheep, goats, dogs, cats or rodents), primates and humans. Preferably, the S100P is human.

In the present invention, "human S100P" is understood as the protein defined by the sequence of the Swiss-Prot database with accession number P25815, corresponding to the sequence of the human S100P protein (SEQ ID NO:1).

```
                                                    SEQ ID NO: 1
MTELETAMGM IIDVFSRYSG SEGSTQTLTK GELKVLMEKE LPGFLQSGKD KDAVDKLLKD 60

LDANGDAQVD FSEFIVFVAA ITSACHKYFE KAGLK                        95
```

The first aspect of the invention contemplates the use of functionally equivalent variants of S100P. As it is used herein, "functionally equivalent variant of S100P" is understood as any molecule sharing with S100P one or more of the functions described in the present invention associated with S100P, both in vitro an in vivo, and having a minimal identity in the amino acid sequence. The variants of S100P can be both natural and artificial.

The expression "natural variant" refers to all those variants of human S100P mentioned above which occur naturally in other species, i.e., S100P orthologs. Said natural variants include but are not limited to S100P of macaque monkeys, corresponding to the predicted sequence with accession number XP_001091876; S100P of chimpanzees, corresponding to the predicted sequence with accession number XP_001156309; S100P of rabbits, corresponding to the predicted sequence with accession number XP_002724365. The natural variants of S100P suitable for use in the first aspect of the present invention can also be derived from said sequences by means of insertion, substitution or deletion of one or more amino acids and include natural alleles, variants resulting from alternative processing and secreted and truncated forms occurring naturally.

The S100P useful in the present invention can, therefore, be of a natural sequence when it comprises a polypeptide having the same amino acid sequence as the S100P derived from nature. Such polypeptides of a natural sequence can be isolated from nature or they can be produced by recombinant and/or synthetic means. Thus, the S100P of the invention can be a recombinant protein obtained by the expression of a polynucleotide encoding S100P or a functionally equivalent variant thereof in a heterologous organism, such as a bacterium, yeast or insect or mammal cell. Said recombinant protein can be obtained as a fusion protein with an amino-terminus tail of histidines facilitating the subsequent purification thereof. The expression and purification of said proteins can be performed according to methods known by the person skilled in the art and described in the state of the art.

In a preferred embodiment, the S100P is of a human origin, preferably of sequence SEQ ID NO:1. In another preferred embodiment, the S100P comes from the expression of a fusion protein comprising the sequence of human S100P with an amino-terminus tail of three additional amino acids, the sequence of which is SEQ ID NO:2.

```
                                                    SEQ ID NO: 2
GSH MTELETAMGM IIDVFSRYSG SEGSTQTLTK GELKVLMEKE

LPGFLQSGKD KDAVDKLLKD LDANGDAQVD FSEFIVFVAA

ITSACHKYFE KAGLK
```

Alternatively, the S100P can be an artificial functionally equivalent variant of S100P which can be obtained by recombinant and/or synthetic means.

The variants of S100P contemplated in the first aspect of the present invention show at least one of the functions of S100P such as, without limitation:

the capacity for inducing tumor cell proliferation, which can be determined by means of the method described in Example 6 of the present invention.

the capacity for stimulating the invasive and metastatic capacity of tumor cells, which can be determined by means of methods described in the state of the art, such as an stimulus-directed invasion using invasion chambers coated with matrigel or by performing orthotopic tumor growth models in mice (Arumugam T et al. 2006. J. Nat. Cancer Inst. 98:1806-1818).

the establishment of the resistance to chemotherapy treatments, which can be determined by means of methods described in the state of the art, such as protection against apoptosis induced by 5-FU in pancreatic cancer (Arumugam T et al., 2005. Clin. Cancer Res. 11:5356-5364) or to camptothecin in prostate cancer (Basu G D et al. 2008. Int. J. Cancer. 123:330-339).

Additionally, the functionally equivalent variants of S100P contemplated in the first aspect of the invention, include polypeptides showing at least 60%, 65%, 70%, 72%, 74%, 76%, 78%, 80%, 90%, 95%, 97%, 99% similarity or identity with the different natural variants of S100P mentioned above. The degree of identity between two polypeptides is determined using algorithms implemented in a computer and methods which are widely known by the persons skilled in the art. The identity between two amino acid sequences is preferably determined using the BLASTP algorithm (BLAST Manual, Altschul, S. et al., NCBI NLM NIH Bethesda, Md. 20894, Altschul, S., et al., J., 1990, Mol. Biol. 215:403-410).

In the context of the present invention, the term "antigen" refers to S100P.

In general, modifications in the amino acid sequence of the antibody of the invention are also contemplated. For example, it can be desirable to improve the binding affinity and/or other biological properties of the antibody. The variants of the amino acid sequences of the antibody are prepared by introducing the suitable nucleotide changes in the nucleic acid encoding the antibody, or by means of peptide synthesis. Said modifications include, for example, eliminations and/or insertions and/or substitutions of residues in the amino acid sequences of the antibody. Any combination of elimination, insertion and substitution is performed to achieve the final construct, provided that the final construct has the desired characteristics, i.e., S100P binding specificity and antagonist activity of said protein. The changes in the amino acids can also alter the post-translational processes of the antibody, such as changing the number or the position of the sites of glycosylation.

Some insertions in the amino acid sequence include amino terminus and/or carboxy terminus fusions varying in length from one residue up to polypeptides containing one hundred or more residues, as well as insertions within the sequence of one or several amino acid residues. Some examples of terminal insertions include an antibody with an N-terminus methionyl residue, or the antibody fused to a cytotoxic polypeptide. Other variants by insertion of the antibody molecule include fusion with the N- or C-terminus of the antibody of an enzyme, or a polypeptide increasing the serum half-life of the antibody.

Another type of variant is a variant by amino acid substitution. These variants have at least one amino acid residue of the antibody substituted with a different residue. The sites of major interest for mutagenesis by antibody substitution include the hypervariable regions, but alterations in the FR are also contemplated.

"Medicament" is understood as a pharmaceutical composition comprising an antibody which binds specifically to the S100P protein or a fragment thereof with capacity for binding to the antigen.

"Prevention" is understood as the administration of an antibody which binds specifically to the S100P protein or of a fragment thereof with capacity for binding to the antigen, or of a medicament containing them in an initial or early stage of the disease, or to also prevent its onset.

The term "treatment" is used to designate the administration of an antibody which binds specifically to the S100P protein or of a fragment thereof with capacity for binding to the antigen or of a medicament containing it to control the progression of the disease before or after the clinical signs have appeared. Control of the progression of the disease is understood as the beneficial or desired clinical results which include but are not limited to reduction of the symptoms, reduction of the duration of the disease, stabilization of pathological conditions (specifically avoiding additional impairment), delaying the progression of the disease, improving the pathological condition and remission (both partial and complete). The control of the progression of the disease also involves a prolongation of survival in comparison to the expected survival if the treatment was not applied.

The terms "cancer" and "tumor" relate to the physiological condition in mammals characterized by unregulated cell growth. The antibodies binding specifically to the S100P protein or its fragments with capacity for binding to the antigen are useful for the treatment of any cancer or tumor, such as, without limitation, breast, heart, lung, small intestine, colon, splenic, kidney, bladder, head, neck, ovarian, prostate, brain, pancreatic, skin, bone, bone marrow, blood, thymic, uterine, testicular and liver tumors. Particularly, tumors which can be treated with said antibodies include but are not limited to adenoma, angiosarcoma, astrocytoma, epithelial carcinoma, germinoma, glioblastoma, glioma, hemangioendothelioma, hemangiosarcoma, hematoma, hepatoblastoma, leukemia, lymphoma, medulloblastoma, melanoma, neuroblastoma, osteosarcoma, retinoblastoma, rhabdomyosarcoma, sarcoma and teratoma. Particularly, the tumor/cancer is selected from the group of acral lentiginous melanoma, actinic keratosis adenocarcinoma, adenoid cystic carcinoma, adenomas, adenosarcoma, adenosquamous carcinoma, astrocytic tumors, Bartholin gland carcinoma, basal cell carcinoma, bronchial gland carcinoma, capillary carcinoid, carcinoma, carcinosarcoma, cholangiocarcinoma, cystadenoma, endodermal sinus tumor, endometrial hyperplasia, endometrial stromal sarcoma, endometrioid adenocarcinoma, ependymal sarcoma, sarcoma de Ewing, focal nodular hyperplasia, germ-line tumors, glioblastoma, glucagonoma, hemagioblastoma, hemangioendothelioma, hemangioma, hepatic adenoma, hepatic adenomatosis, hepatocellular carcinoma, insulinoma, intraepithelial neoplasia, interepithelial squamous cell neoplasia, invasive squamous cell carcinoma, large-cell carcinoma, leiomyosarcoma, melanoma, malignant melanoma, malignant mesothelial tumor, medulloblastoma, medulloepithelioma, mucoepidermoid carcinoma, neuroblastoma, neuroepithelial adenocarcinoma, nodular melanoma, osteosarcoma, papillary serous adenocarcinoma, pituitary tumors, plasmacytoma, pseudosarcoma, pulmonary blastoma, renal cell carcinoma, retinoblastoma, rhabdomyosarcoma, sarcoma, serous carcinoma, small-cell carcinoma, soft tissue carcinoma, somatostatin secreting tumor, squamous carcinoma, squamous cell carcinoma, undifferentiated carcinoma, uveal melanoma, verrucous carcinoma, vipoma, Wilm's tumor. In a preferred embodiment of the invention, the tumor/cancer to be prevented or treated with said antibodies is any cancer with the exception of pancreatic cancer and colon cancer. In another preferred embodiment of the invention, the tumor/cancer to be prevented or treated with said antibodies is pancreatic cancer, preferably pancreatic adenocarcinoma.

"Pancreatic adenocarcinoma" is understood as a cancerous tumor originating in the cells lining the pancreatic duct.

In another preferred embodiment of the invention, the tumor/cancer to be prevented or treated with said antibodies is fibrosarcoma.

As used herein, the term "fibrosarcoma" refers to a malignant tumor composed of cells and fibers derived from fibroblasts, which produce collagen but otherwise lack cellular differentiation.

It is known that the S100P protein is involved in the establishment of resistances to chemotherapy treatments. Therefore, in a particular embodiment the cancer to be prevented or treated is a cancer resistant to chemotherapy treatment.

"Cancer resistant to chemotherapy treatment" is understood as a cancer which does not respond to treatment or loses or shows a reduced response over the course of cancer therapy to a conventional chemotherapy.

It is known that the S100P protein is also useful for reducing metastatic progression of cancer. Therefore, in a particular embodiment the cancer to be prevented or treated is a metastatic cancer resistant.

As used herein, the term "metastatic" refers to a cancer for which there is known to exist at least one tumor (a "secondary tumor") in an organ other than the organ which is the source of the tumor cells. For example, colorectal cancer has a tendency to spread from the colon or rectum to lymph nodes and then to the liver. The organ which is the source of the tumor cells can be identified using standard methods in the art.

In one embodiment of the present invention, the medicament comprises one or more antibodies according to the invention as the sole therapeutic agent. However, the medicament of the invention can also contain one or several additional compounds for the treatment of cancer. Therefore, in another embodiment of the present invention, the medicament is prepared for the combined administration of an antibody according to the invention and one or more therapeutic agents useful in the treatment of said disease.

The term "therapeutic agent useful in the treatment of said disease" refers to an agent suitable for being used in the treatment of cancer.

For the treatment of cancer, the antibody of the invention can be used in combination with an additional therapeutically active compound, such as a cytotoxic agent, an antiangiogenic agent or an antimetastatic agent.

Cytotoxic agents which can be used in combination with the antibodies of the invention for the treatment of cancer include but are not limited to anthracycline antibiotics such as doxorubicin and daunorubicin, taxanes such as Taxolm and docetaxel, vinca alkaloids such as vincristine and vinblastine, 5-fluorouracil (5-FU), leucovorin, irinotecan, idarubicin, mitomycin C, oxaliplatin, raltitrexed, tamoxifen, cisplatin, carboplatin, methotrexate, actinomycin D, mitoxantrone, blenoxane or mithramycin. Antiangiogenic agents which can be used in combination with the antibodies of the invention for the treatment of cancer include but are not limited to an antiangiogenic agent selected from the group of paclitaxel, 2-methoxyestradiol, prinomastat, batimastat, BAY 12-9566, carboxyamidotriazole, CC-1088, dextromethorphan acetic acid, dimethylxanthenone acetic acid, endostatin, IM-862, marimastat, penicillamine, PTK787/ZK 222584, RPI.4610, squalamine lactate, SU5416, thalidomide, combretastatin, tamoxifen, COL-3, neovastat, BMS-275291, SU6668, anti-VEGF antibodies, Medi-522 (Vitaxin II), CAI, interleukin 12, IM862, amiloride, angiostatin, Kl-3 angiostatin, Kl-5 angiostatin, Captopril, DL-alpha-difluoromethylornithine, DL-alpha-difluoromethylornithine HCl, endostatin, fumagillin, herbimycin A, 4-hydroxyphenylretinamide, jugione, laminin, laminin hexapeptide, laminin pentapeptide, lavendustin A, medroxyprogesterone, minocycline, placenta ribonuclease inhibitor, suramin, thrombospondin, antibodies directed against proangiogenic factors (for example, Avastin, Erbitux, Vectibix, Herceptin); low molecular weight tyrosine kinase inhibitors of proangiogenic growth. factors (for example Tarceva, Nexavar, Sutent, Iressa); mTOR inhibitors (for example Torisel); interferon alpha, beta and gamma, IL-12, matrix metalloproteinase inhibitors (for example, COL3, marimastat, batimastat); ZD6474, SU11248, vitaxin; PDGFR inhibitors (for example Gleevec); NM3 and 2-ME2; cyclopeptides such as cilengitide. Antimetastatic agents which can be used in combination with the antibodies of the invention for the treatment of cancer include but are not limited to any agent capable of acting as an antimetastatic agent, such as alkylating agents; antimetabolites such as 5-fluorouracil, pemetrexed (MTA), raltitrexed (TDX); platinum cytotoxic agents such as cisplatin or oxaliplatin; topoisomerase inhibitors; antimicrotubule agents; anthracyclines; plant alkaloids; GTPase inhibitors; angiogenesis inhibitors; matrix metalloproteinase inhibitors; inhibitors of the cell cycle regulating kinase, such as cyclin-dependent kinases and cyclin inhibitors; Wnt signaling inhibitors; inhibitors of the E2F transcription factor; histone deacetylase inhibitors; AKT kinase or ATPase inhibitors.

As "Combined administration" it is understood that the antibody according to the invention is administered jointly or separately, simultaneously, at the same time or sequentially with a therapeutic agent useful in the treatment of cancer in any order. For example, the administration of the antibody of the invention can be done first, followed by the administration of one or more therapeutic agents useful in the treatment of said pathology; or the administration of the antibody of the invention can be done last, preceded by the administration of one or more therapeutic agents useful in the treatment of said pathology; or the administration of the antibody of the invention can be done at the same time as the administration of one or more therapeutic agents useful in the treatment of said pathology.

The person skilled in the art will understand that in the context of the present invention, the medicament for the combined administration of an antibody according to the invention and an additional therapeutic agent useful in the treatment of cancer can be prepared as a single dosage form or in separate dosage forms.

In a particular embodiment, the antibody used is a monoclonal antibody produced by a hybridoma selected from the group consisting of ECACC 10121601, ECACC 10121602, ECACC 10121603 and ECACC 10121604 or a functional variant of said antibody as will later be described in the context of the monoclonal antibodies of the invention.

The terms "monoclonal antibody" and "hybridoma" are defined below in the context of the second aspect of the invention.

"Functional variant" of the monoclonal antibodies of the invention is understood as any molecule sharing with said monoclonal antibodies one or more of the functions described in the present invention associated with said monoclonal antibodies, both in vitro an in vivo, and having a minimal identity in the amino acid sequence. The functional variants of the monoclonal antibodies of the invention can be derived from said sequences by means of insertion, substitution or deletion of one or more amino acids and can be obtained by recombinant and/or synthetic means.

The functional variants of the monoclonal antibodies of the invention must conserve their capacity for binding to the S100P antigen and also the capacity for inhibiting one or more characteristic functions of the S100P protein, such as the interaction of the S100P protein with one or more of its ligands, especially with its RAGE ligand, and/or the inhibition of one or more of the functions mediated by S100P, such as the tumor cell proliferation. Said functions can be determined by means of the methods described in the examples of the present invention.

The functional variants of the monoclonal antibodies of the invention include polypeptides showing at least 60%, 65%, 70%, 72%, 74%, 76%, 78%, 80%, 90%, 95%, 97%, 99% similarity or identity with the polypeptide sequence of said antibodies. The degree of identity between two polypeptides is determined using algorithms implemented in a computer and methods which are widely known by the persons skilled in the art. The identity between two amino acid sequences is preferably determined using the BLASTP algorithm (BLAST Manual, Altschul, S. et al., NCBI NLM NIH Bethesda, Md. 20894, Altschul, S., et al., J., 1990, Mol. Biol. 215:403-410).

Monoclonal Antibodies of the Invention

In a second aspect, the invention relates to a specific anti-S100P monoclonal antibody produced by a hybridoma selected from the group of ECACC 10121601, ECACC 10121602, ECACC 10121603 and ECACC 10121604 or a polypeptide having at least one fragment of the sequence of said monoclonal antibody with capacity for binding to S100P.

As it is used herein, the term "antibody" refers to an immunoglobulin showing specific binding activity towards a target molecule or antigen, which in this specific case is the S100P protein.

In the present document, the "antigen" is the molecule to which an antibody specifically binds. Specifically, the antigen for the antibodies of the invention is the S100P protein.

The antibodies of the invention are capable of binding to an epitope of the S100P protein. The term "epitope" or "antigenic determinant" includes any region of an antigen which is specifically recognized by an antibody. One and the same antigen can have different epitopes. Each epitope usually consists of clusters of chemically active surfaces of molecules such as amino acids or sugar side chains, which have specific three-dimensional structural characteristics, as well as specific charge characteristics. At least 6, 8, 10 or 12 contiguous amino acids are typically required to form an epitope. However, the epitopes involving non-contiguous amino acids may require more, for example, at least 15, 25 or 50 amino acids.

In the context of this second aspect, a "specific anti-S100P monoclonal antibody" is a homogenous antibody produced by a hybrid cell or hybridoma which is capable of specifically recognizing a specific epitope of the S100P protein, but it does not recognize other proteins of the S100 family. The monoclonal antibodies of the invention preferably recognize human S100P, but they can also recognize the S100P protein of other mammal species as has been described in the context of the first aspect of the invention. In preferred embodiments of the invention, the monoclonal antibody is any of those mentioned in this second aspect of the invention.

The term S100P has been defined in the context of the first aspect of the invention and also includes the functionally equivalent variants of S100P.

In the context of the present invention, "hybrid cell" or "hybridoma" is understood as the product of the fusion of a B-cell clone descendent of a single unique stem cell, and of a myeloma cell. Specifically, the monoclonal antibodies of the second aspect of the invention correspond with the anti-S100P monoclonal antibodies referred to in the experimental part of the present document as 1A5, 3E3, 2H8 and 3F8, which have been obtained from the hybridomas generated by the inventors and identified as 1A5-2G8-2D1, 3E3-2A2-5H9, 2H8-3A4-2D3 and 3F8-1A9-2G8, respectively. Said hybridomas have been deposited prior to filing the present patent application in the European Collection of Cell Cultures (ECACC), Porton Down, Salisbury, SP4 OJG, United Kingdom, as a legally recognized institution for that purpose in accordance with the Budapest Treaty, of 28 Apr. 1977, on the International Recognition of the Deposit of Microorganisms.

The European Collection of Cell Cultures (ECACC) has assigned to hybridomas 1A5-2G8-2D1, 3E3-2A2-5H9, 2H8-3A4-2D3 and 3F8-1A9-2G8 the respective deposit numbers ECACC 10121601, ECACC 10121602, ECACC 10121603 and ECACC 10121604. The culture conditions of said hybridoma lines which allow obtaining the anti-S100P monoclonal antibodies of the invention are described in the context of the method for obtaining the monoclonal antibodies of the invention.

In the present document, hybridomas 1A5-2G8-2D1, 3E3-2A2-5H9, 2H8-3A4-2D3 and 3F8-1A9-2G8 and the antibodies produced by said hybridomas are indicated by means of their abbreviated name 1A5, 3E3, 2H8 and 3F8, respectively.

The invention also contemplates polypeptides having at least one fragment of the sequence of the specific anti-S100P monoclonal antibodies of the second aspect of the invention which maintain the capacity for binding to S100P. Said capacity for binding can be checked by means of methods known by the person skilled in the art, such as ELISA or Western blot, as described in Examples 4 and 5 of the present invention.

"Polypeptides" are understood as molecules formed by the binding of at least 10 amino acids by means of peptide bonds. The polypeptides of the invention must have at least one fragment of the sequence of the mentioned specific anti-S100P monoclonal antibodies. Said "fragment of the sequence" can correspond to one or several portions of the amino acid sequence of the mentioned monoclonal antibody which maintains the capacity for binding to S100P, and therefore, the polypeptide must include the sequence of the 6 CDR regions, which can be used for obtaining the antibodies defined in the context of the first aspect of the invention, such as, without limitation, genetically engineered antibodies such as chimeric antibodies, humanized antibodies or bispecific antibodies. Said "fragment of the sequence" can also be used for obtaining antibody fragments such as Fab, F(ab')2, Fab', single chain Fv fragments (scFv), diabodies or nanobodies.

The Fab and F(ab')2 fragments can be obtained by means of enzymatic or chemical cleavage of the intact monoclonal antibodies of the second aspect of the invention.

Papain digestion of a monoclonal antibody of the invention produces two identical antigen binding fragments referred to as "Fab" fragments, each with a single antigen binding site. In turn, the "F(ab')2" fragment, which has two antigen binding sites, is obtained by pepsin treatment.

Additionally, the "fragment of the sequence" allows obtaining another type of antibody fragments such as Fab' fragments, single chain Fv fragments (scFv) or diabodies by means of genetic engineering techniques.

The monoclonal antibodies of the second aspect of the invention have demonstrated that they are capable of neutralizing tumor cell proliferation. Therefore, in a particular embodiment, the invention relates to a monoclonal antibody produced by a hybridoma selected from ECACC 10121601, ECACC 10121602, ECACC 10121603 and ECACC 10121604 or a polypeptide having at least one fragment of the sequence of said monoclonal antibody which is capable of stopping the growth of tumor cells.

"Stopping the growth of tumor cells" is understood as the inhibition of the proliferation of said tumor cells by at least 25%, 30%, 35%, 40%, 45%, 50%, 60%, 70%, 75%, 80%, 85%, 90%, 95%, 99%, 100%; preferably at least 80%; more preferably at least 85%; still more preferably at least 90%; most preferably at least 95%. Said inhibition of the proliferation or stop of the growth can be evaluated by means of the assays described in Example 6 of the present invention.

"Tumor cell" is understood as a malignant cell, also known as a cancerous or carcinogenic cell which grows and divides beyond the normal limits, invading the surrounding tissue and sometimes causing metastasis. The tumor cells that can be treated with the antibodies of the present invention are cells which overexpress the S100P protein. Said cells include tumor cells from known and established cell lines and tumor cells present in the organism of a patient suffering from cancer. Several illustrative non-limiting examples of known tumor lines which overexpress S100P are the BxPC3 pancreatic adenocarcinoma tumor line (Arumugam T et al. Clin Cancer Res 2005. 11(15):5356-64), cervical epithelioid carcinoma HeLa tumor line (Dowen S E et al. Am J Pathol 2005. 166(1): 81-92), Colo 205 colon adenocarcinoma tumor line (reference in the Genome Anatomy Project Cancer database: NCI), T47D breast adenocarcinoma cell line (Beissel B et al. Oncol Rep 2007. 17: 611-615) and PC3 prostate adenocarcinoma cell line (Basu G D et al. Int J Cancer 2008. 123: 330-339). Illustrative non-limiting examples of tumor cells present in a patient suffering from cancer and which overexpress S100P are tumor cells from pancreatic tumors (Logsdon C. D. et al. 2003. Cancer Res, 63:2649-2657), breast tumors (Guerreiro Da Silva I.D. et al. 2000. Int J Oncol, 16:231-240; Wang G. et al. 2006. Cancer Res, 66:1199-1207), colon tumors (Fuentes M. K. et al. 2007. Dis Colon Rectum, 50:1230-1240), prostate tumors (Mousses S. et al. 2002. Cancer Res, 62:1256-1260), lung tumors (Diederichs S. et al. 2004. Cancer Res, 64:5564-5569), ovarian tumors (Surowiak P. et al. 2007. Histopathology, 51:125-128), leukemia tumors (Tsumura H. et al. 2009. Leukemia, 23:753-760), squamous cell carcinoma of the oral cavity (Kupferman M. E. 2007. Oral Oncol, 43:440-454) and cells from gastric tumors (Shyu R. Y. et al. 2003. J Biomed Sci, 10:313-319; Liang J. et al. 2007. Biochem Cell Biol, 85:375-383).

The tumor cells which express the S100P protein can be identified by means of conventional methods such as ELISA or Western blot, according to the method described in the present invention.

In one embodiment, the tumor cells the growth of which is stopped by means of the antibodies of the invention are tumor cells of any type of tumor with the exception of pancreatic cancer and colon cancer, preferably with the exception of pancreatic cancer, more preferably with the exception of colon cancer. In another embodiment the tumor cells the growth of which is stopped by means of the antibodies of the invention are pancreatic adenocarcinoma tumor cells.

In a particular embodiment, tumor growth is stopped by means of the pre-incubation of the monoclonal antibody to be used with the S100P protein before subjecting the cell, tissue or organism to treatment with the combination of this protein and said monoclonal antibody.

The antibodies of the invention are also capable of showing antimetastatic activity. Thus, in a preferred embodiment the monoclonal antibody or polypeptide according to the invention is antimetastatic.

"Antimetastatic" is understood as a chemical or biological substance which inhibits or reduces metastasis, i.e., the distance propagation, fundamentally by the lymphatic or blood stream, of the cancer causing cells, and the growth of new tumors in the destination sites of said metastasis. Preferably, the antimetastatic antibody or fragment thereof of the invention is understood as the inhibition of the metastasis of said tumor cells by at least 25%, 30%, 35%, 40%, 45%, 50%, 60%, 70%, 75%, 80%, 85%, 90%, 95%, 99%, 100%; preferably at least 80%; more preferably at least 85%; still more preferably at least 90%; most preferably at least 95%. Said inhibition of the proliferation or stop of the growth can be evaluated by means of the assays described in Example 8 of the present invention.

In another aspect, the invention relates to a specific anti-S100P monoclonal antibody produced by a hybridoma selected from the group of ECACC 10121601, ECACC 10121602, ECACC 10121603 and ECACC 10121604 or a polypeptide having at least one fragment of the sequence of said monoclonal antibody with capacity for binding to S100P for its use in medicine.

Method for Obtaining the Monoclonal Antibodies of the Invention

In another aspect, the invention relates to a method for obtaining a monoclonal antibody according to the second aspect of the invention which comprises culturing a hybridoma cell line selected from those cell lines deposited with accession number ECACC 10121601, ECACC 10121602, ECACC 10121603 and ECACC 10121604 in conditions which allow the production of said antibody.

The method for obtaining the monoclonal antibodies of the second aspect of the invention can be performed according to conventional methods known in the state of the art.

Basically, the method consists of culturing the hybridoma cell line in a culture medium suitable for the hybridoma cells to produce antibodies and to secrete them into the medium, and of subsequently collecting the supernatant of the culture medium containing the monoclonal antibodies produced. Said antibodies can optionally be purified by conventional means, such as affinity chromatography, protein A sepharose, hydroxyapatite chromatography, gel electrophoresis or dialysis.

The term "monoclonal antibody" has already been defined in the previous aspect.

"Culturing" a hybridoma cell line is understood as incubating the hybridoma cells in the presence of a suitable medium in culture vials for the necessary time and in the suitable conditions for the multiplication of said cells and the production of the monoclonal antibodies of the invention to occur. Said culture can involve the use of culture media with different compositions. Preferably, in a first step the cells are cultured in a medium containing serum to favor their multiplication and, after collecting the cells and washing them, they are cultured in a serum-free medium to obtain antibodies. Culture media suitable for obtaining the antibodies according to this method are, without limitation, DMEM/F12 supplemented with L-Glutamine and Fetal Calf Serum to favor cell multiplication and a mixture based on the DMEM/F12 medium supplemented with L-glutamine but lacking Fetal Calf Serum ("protein free medium") as an antibody collection medium. The medium for producing antibodies could also consist of any medium or mixture of synthetic cell culture mediums the composition and subsequent supplementation of which does not include proteins ("protein free medium") or said proteins are in a very low proportion ("serum free medium" or "low protein medium") and they do not belong to the group of immunoglobulins. Said medium must allow the cell growth and maintenance as well as the secretion of antibodies by the hybridoma cell line previously adapted to grow in the absence of Fetal Calf Serum. In a preferred embodiment the medium suitable for the culture of said cells is a medium comprising DMEM/F12 and L-glutamine. The conditions in which said culture are performed are preferably in a humid environment and at a temperature of 37° C. with standard air atmosphere or 5% $CO_2$ enriched air.

Therefore, in another aspect the invention relates to a hybridoma cell line selected from those cell lines deposited with accession number ECACC 10121601, ECACC 10121602, ECACC 10121603 and ECACC 10121604.

The expression "hybridoma cell line" refers to a cell line formed by hybrid cells or hybridomas as previously defined in the second aspect of the invention. Said hybridoma cell line has been obtained by standard methodologies as described in Examples 2 and 3 of the present invention. Briefly, mice were immunized with a human recombinant S100P protein and cells were extracted from the spleen of the immunized mouse which were fused with myeloma cells in the presence of a fusion inducer such as PEG-1500. The hybridomas were selected in HAT medium and each selected clone was subcloned by limiting dilution. The clones suitable for expansion were adapted to the DMEM/F12 medium and were frozen, constituting the hybridoma cell lines ECACC 10121601, ECACC 10121602, ECACC 10121603 and ECACC 10121604.

In preferred embodiments of the invention, the monoclonal antibody prepared by means of this method can be any of those produced by the hybridoma cell lines described in the context of the present invention.

Pharmaceutical Compositions of the Monoclonal Antibodies of the Invention

In another aspect, the invention relates to a pharmaceutical composition comprising a pharmaceutically effective amount of at least one monoclonal antibody according to the second aspect of the invention or a polypeptide having at least one fragment of the sequence of said monoclonal antibody with capacity for binding to S100P and at least one pharmaceutically acceptable excipient.

In a further aspect, the invention relates to a composition comprising, together or separated, an antibody that binds specifically to the S100P protein or of a fragment thereof with capacity for binding to the antigen and a chemotherapeutic agent.

In another preferred embodiment the invention relates to a composition comprising, together or separated, an antibody that binds specifically to the S100P protein or of a fragment thereof with capacity for binding to the antigen and a chemotherapeutic agent for use in the prevention and/or treatment of cancer.

As it is used in the present invention, the expression "pharmaceutical composition" relates to a formulation that has been adapted for administering a predetermined dose of one or several therapeutic useful agents to a cell, a group of cells, an organ, a tissue or an animal in which there is an overexpression of the S100P protein.

"Pharmaceutically effective amount" is understood as an amount capable of providing a therapeutic effect, and which can be determined by the person skilled in the art by commonly used means.

The compositions of the invention can contain one or more monoclonal antibodies according to the second aspect of the invention or one or more polypeptides having at least one fragment of the sequence of said monoclonal antibodies with capacity for binding to S100P.

The compositions of the invention can also contain one or several additional compounds for the prevention and/or treatment of pathologies in which there is an overexpression of the S100P protein, such as cancer. Said additional compounds such as cytotoxic agents, antiangiogenic agents or antimetastatic agents can form part of the pharmaceutical composition as independent entities of the monoclonal antibodies or also forming conjugates with said antibodies.

The pharmaceutical compositions are prepared by conventional means with one or more pharmaceutically acceptable excipients.

"Pharmaceutically acceptable excipient" is understood a therapeutically inactive substance said to be used for incorporating the active ingredient and which is acceptable for the patient from a pharmacological/toxicological point of view and for the pharmaceutical chemist who manufactures it from a physical/chemical point of view with respect to the composition, formulation, stability, acceptation of the patient and bioavailability.

The number and the nature of the pharmaceutically acceptable excipients depend on the desired dosage form. The pharmaceutically acceptable excipients are known by the person skilled in the art (Faulí y Trillo C. (1993) "Tratado de Farmacia Galénica", Luzán 5, S. A. Ediciones, Madrid). Said compositions can be prepared by means of the conventional methods known in the state of the art ("Remington: The Science and Practice of Pharmacy", 20$^{th}$ edition (2003) Genaro A. R., ed., Lippincott Williams & Wilkins, Philadelphia, US).

The pharmaceutical compositions containing a monoclonal antibody according to the second aspect of the invention or a polypeptide having at least one fragment of the sequence of said monoclonal antibodies with capacity for binding to S100P can be administered by any type of suitable route, such as by oral route, topical route, by inhalation or parenteral route so that the pharmaceutically acceptable excipients necessary for the formulation of the desired dosage form will be included. The preferred route of administration of the pharmaceutical composition is the endovenous route.

"Oral route" is understood as the pharmaceutical composition incorporated into the organism after deglutition. In a particular embodiment, the pharmaceutical composition of the invention can be in a dosage form suitable for its administration by oral route, whether it is solid or liquid. The dosage forms suitable for their administration by oral route can be tablets, capsules, syrups or solutions, and can contain any conventional excipient known in the art, such as binders, for example syrup, acacia, gelatin, sorbitol or polyvinylpyrrolidone; filling agents, for example lactose, sugar, corn starch, calcium phosphate, sorbitol or glycine; lubricants for compression, for example, magnesium stearate; disintegrating agents, for example starch, polyvinylpyrrolidone, sodium glycolate of starch or microcrystalline cellulose; or pharmaceutically acceptable wetting agents such as sodium lauryl sulfate. The solid oral compositions can be prepared by means of conventional processes of mixing, filling or compressing. Repetitive mixing operations can be used to completely distribute the active agent in those compositions that use high amounts of filling agents. Said operations are conventional in the art. The tablets can be prepared, for example, by means of wet or dry granulation, and optionally coating them according to the processes known in the common pharmaceutical practice, particularly with an enteric coating.

On the other hand, "topical route" is understood as an administration by non-systemic route, and includes the application of a pharmaceutical composition of the invention externally on the epidermis, in the oral cavity and the instillation of said composition into ears, eyes and nose, and in which it does not significantly enter the blood stream. "Systemic route" is understood as the administration by oral route, intravenous route, intraperitoneal route and intramuscular route. The amount of antibody required for the therapeutic or prophylactic effect will naturally vary according to the elected antibody, the nature and the severity of the illness that is going to be treated, and the patient.

"Inhalation" is understood as the administration by intranasal route and by oral inhalation. The dosage forms suitable for said administration, such as a formulation in aerosol or a meter dosed inhaler can be prepared by means of conventional techniques.

As it is used herein, the term "parenteral", includes administration by intravenous route, intraperitoneal route, intramuscular route or subcutaneous route. Subcutaneous, intramuscular and intravenous dosage forms of parenteral administration are generally preferred.

In one embodiment, the pharmaceutical compositions of the invention can be adapted for their parenteral administration, such as sterile solutions, suspensions or lyophilized products in the appropriate dosage unit form. The pharmaceutical compositions suitable for its injectable use include sterile aqueous solutions (when they are soluble in water), or dispersions and sterile powders for the extemporaneous preparation of sterile injectable solutions or dispersions. For its administration by intravenous route, some suitable carriers include saline solution buffered with phosphate (PBS). In all the cases, the composition must be sterile, and must be fluid to the point which that there exists easy ability for being injected. It must be stable in the preparation and storage conditions, and must be protected from the contamination action of microorganisms such as bacteria and fungi. The carrier can be a solvent or a dispersion medium which contains, for example, water, ethanol, a pharmaceutically acceptable polyol such as glycerol, propylene glycol, liquid polyethylene glycol and suitable mixtures thereof. Suitable fluidity can be maintained, for example, by means of using a coating such as lecithin, by means of maintaining the particle size required in the case of a dispersion and by means of using surfactants. The prevention of the action of the microorganisms can be achieved by means of various antibacterial and antifungal agents, for example, parabens, chlorobutanol, phenol, ascorbic acid, thiomersal, and the like. In most cases, it will be preferable to include isotonic agents, for example, sugars; polyalcohols such as mannitol, sorbitol; or sodium chloride in the composition. The prolonged absorption of the injectable compositions may be caused by the inclusion of an agent which delays the absorption, for example, aluminum and gelatin monostearate.

The injectable sterile solutions can be prepared by incorporating the active compound in the required amount in a suitable solvent with one or a combination of the aforementioned ingredients, as needed, followed by sterilization by filtration through sterile membranes. Generally, the dispersions are prepared by incorporating the active compound in a sterile vehicle containing a basic dispersion medium and the rest of the ingredients required from among those previously listed. In the case of sterile powders for the preparation of injectable sterile solutions, the preferred preparation processes are vacuum drying and lyophilization which give rise to a powder with the active ingredient plus any desired additional ingredient from a previously filtered sterile solution thereof. The antibody will usually be stored in lyophilized form or in solution. The compositions of therapeutic antibody are generally housed in a packaging which has a sterile access opening, for example, an intravenous solution bag or vial having an adaptor which allows recovering the formulation, such as a stopper that can be perforated by a hypodermic injection needle.

The pharmaceutical composition can be suitably administered by means of pulse infusion, for example, with decreasing doses of the antibody. Preferably, the dose is administered by means of injections, more preferably intravenous or subcutaneous injections, partly depending if the administration is acute or chronic.

In one embodiment, the pharmaceutical composition which contains the antibody of the second aspect of the invention is prepared with carriers which will protect said antibody from a rapid elimination from the body, such as a controlled release formulation, including implants and microencapsulated administration systems. Biodegradable biocompatible polymers such as ethylene vinylacetate, polyanhydrides, polyglycolic acid, collagen, polyorthoesters and polylactic acid can be used. The processes for preparing said formulations will be clear for persons skilled in the art. The materials can also be commercially obtained in Alza Corporation and Nova Pharmaceuticals, Inc.

The sustained release compositions also include preparations of antibody crystals suspended in suitable formulations which can maintain the crystals in suspension. These preparations, when they are injected by subcutaneous or intraperitoneal route may produce a sustained release effect. Other compositions also include antibodies trapped in liposomes. The liposomes containing such antibodies are prepared by means of known methods such as Epstein et al., Proc. Natl. Acad. Sci. USA, (1985) 82:3688-3692; Hwang et al., Proc. Natl. Acad. Sci. USA, (1980) 77:4030-4034; EP 52,322; EP 36,676; EP 88,046; EP 143,949.

The compositions of the invention are suitable for the administration into any type of mammal, preferably a human being.

In a particular embodiment the pharmaceutical composition of the invention comprises of, additionally, the S100P protein.

The term "chemotherapeutic agent" refers to a cytotoxic agent, an antiangiogenic agent or an antimetastatic agent as previously described. In a more preferred embodiment, the chemotherapeutic agent is an inhibitor of topoisomerase I or II.

"Topoisomerase I and II inhibitors" are agents designed to interfere with the action of topoisomerase enzymes I and II. Topoisomerase I inhibitors include, without limitation, irinotecan, topotecan, camptothecin, acetylcamptothecin, 9-aminocamptothecin, lamellarin D and betulinic acid. Toposomerase II inhibitors include, without limitation, amsacrine, etoposide, teniposide and doxorubicin. In a preferred embodiment the topoisomerase I and II inhibitor is doxorubicin.

The composition of a antibody according to the invention and a chemotherapeutic agent is capable of reducing the viability of tumor cells.

"Reducing the viability of tumor cells" is understood as the reduction of the capacity of the cells to survive, grow and multiply by at least 30%, 40%, 50%, 60%, 65%, 70%, 75%, 80%, 85%, 90%, 95%, 99%, 100%; preferably at least 60%; still more preferably at least 65%; most preferably at least 70%. Said reduction of the viability can be evaluated by means of the assay described in Example 11 of the present invention.

Thus, in another aspect, the invention relates to a composition according to the invention for use in the prevention and/or treatment of cancer.

In another preferred embodiment of the invention, the tumor/cancer to be prevented or treated with said antibodies is pancreatic cancer, preferably pancreatic adenocarcinoma. In another preferred embodiment of the invention, the tumor/cancer to be prevented or treated with said antibodies is fibrosarcoma.

Conjugates of the Monoclonal Antibodies of the Invention and their Uses

Given that the monoclonal antibodies of the invention are capable of binding to the S100P protein and that this protein is overexpressed in cancer, the monoclonal antibodies produced by a hybridoma selected from the group consisting of ECACC 10121601, ECACC 10121602, ECACC 10121603 and ECACC 10121604 or a polypeptide having at least one fragment of the sequence of said monoclonal antibody with capacity for binding to S100P constitute agents suitable for carrying compounds with therapeutic activity towards the expression sites of S100P.

The S100P protein is expressed, as has been detailed above, in a great variety of cancers.

Therefore, in another aspect, the invention relates to a conjugate comprising a monoclonal antibody produced by a hybridoma selected from ECACC 10121601, ECACC 10121602, ECACC 10121603 and ECACC 10121604 or a polypeptide having at least one fragment of the sequence of said monoclonal antibody and a second component selected from the group of:
  a) a cytotoxic agent,
  b) an antiangiogenic agent,
  c) an antimetastatic agent "Conjugate" in the context of the present invention is understood as an assembly formed by an antibody according to the second aspect of the invention bound, linked or associated to at least one second component.

The terms "monoclonal antibody", "hybridoma", "polypeptide" and "fragment of the sequence" have been defined in the context of the second aspect of the invention.

"Second component" is understood as a molecule with therapeutic activity which is directed to its action site by means of the monoclonal antibody of the invention.

The S100P protein is overexpressed in tumor cells. Therefore, the monoclonal antibodies of the invention can be used to direct antitumor drugs to the expression sites.

As used in the present invention, the term "cytotoxic agent" relates to an agent which is capable of promoting cell death and which has capacity for reducing the growth, stopping the growth or destroying cells and, particularly, rapidly proliferating cells and, yet more particularly, tumor cells. Cell death can be caused by any mechanism, such as for example apoptosis, although it is not limited to this cause, by the metabolism inhibition, the interference with the organization of the cytoskeleton or the chemical modification of the DNA. The term cytotoxic agent comprises any chemotherapy agent including small organic molecules, peptides, oligonucleotides and the like; toxins; enzymes; cytokines; radioisotopes or radiotherapy agents.

"Chemotherapy agents" are understood as chemical compounds such as, without limitation, anthracycline antibiotics such as doxorubicin and daunorubicin, taxanes such as Taxol™ and docetaxel, vinca alkaloids such as vincristine and vinblastine, 5-fluorouracil (5-FU), leucovorin, irinotecan, idarubicin, mitomycin C, oxaliplatin, raltitrexed, tamoxifen, cisplatin, carboplatin, methotrexate, actinomycin D, mitoxantrone, blenoxane or mithramycin.

"Toxin" is understood as a toxic agent which conjugates with the monoclonal antibody of the invention forming an immunotoxin. The conjugation of determined toxins with antibodies reduces the toxicity of the former, enabling their use as therapeutic agents, because otherwise they would be too toxic. The binding between the toxin and the antibody is performed chemically, conserving its biological activity. Their separation generally occurs in the lysosomes of the target cells recognized by the antibody such that the mentioned chemical binding is only broken in the enclosed acidic cellular environment provided by the lysosomes. Toxins useful in the context of the present invention are plant toxins, bacterial toxins, toxins of fungal or animal origin and fragments thereof, such as, without limitation, the ricin A-chain, saponin, the diphtheria A-chain, active nonbinding fragments of the diphtheria toxin, *Pseudomonas aeruginosa* exotoxin A-chain, abrin A-chain, modecin A-chain, α-sarcin, *Leurites fordii* A-proteins, dianthin proteins, *Phytolaca americana* (PAPI, PAPII and PAP-S) proteins, *Momordica charantia* inhibitor, curcine, crotin, *Saponaria officinalis* inhibitor, gelonin, mitogelin, restrictocin, phenomycin, enomycin and trichothecenes.

"Enzymes" are understood in the context of the present invention as toxin or drug activating enzymes, such as, without limitation, alkaline phosphatase which activates etoposide and doxorubicin; carboxypeptidase G2 which activates nitrogen mustards; beta-lactamase which activates doxorubicin, paclitaxel and mitomycin.

"Cytokines" are understood as peptides of different sizes and molecular weights which synthesize the cells of the immune system for the purpose of regulating the immune response, and they can be hormones, growth factors, necrosis factors, etc. They can be of natural origin or from recombinant cell cultures and biologically active equivalents of natural sequence cytokines. Their conjugation with antibodies gives rise to immunocytokines. Cytokines useful in the present invention are, without limitation, TNF factor alpha, INF-gamma, GM-GSF factor or IL-2.

"Radioisotopes" is understood as radioactive isotopes such as, without limitation, $^{131}$I, $^{90}$Y, $^{177}$Lu, $^{188}$Re, $^{67}$Cu, $^{211}$At, $^{213}$Bi, $^{125}$I, $^{11}$In.

"Antiangiogenic agent" is understood as a chemical or biological substance which inhibits or reduces the formation of new blood vessels, i.e., angiogenesis.

Antiangiogenic agents that can be conjugated with the antibodies of the invention include, without limitation, an antiangiogenic agent selected from the group of paclitaxel, 2-methoxyestradiol, prinomastat, batimastat, BAY 12-9566, carboxyamidotriazole, CC-1088, dextromethorphan. acetic acid, dimethylxanthenone acetic acid, endostatin, IM-862, marimastat, penicillamine, PTK787/ZK 222584, RPI.4610, squalamine lactate, SU5416, thalidomide, combretastatin, tamoxifen, COL-3, neovastat, BMS-275291, SU6668, anti-VEGF antibodies, Medi-522 (Vitaxin II), CAI, interleukin 12, IM862, amiloride, angiostatin, Kl-3 angiostatin, Kl-5 angiostatin, Captopril, DL-alpha-difluoromethylornithine, DL-alpha-difluoromethylornithine HCl, endostatin, fumagillin, herbimycin A, 4-Hydroxyphenylretinamide, jugione, laminin, laminin hexapeptide, laminin pentapeptide, lavendustin A, medroxyprogesterone, minocycline, placenta ribonuclease inhibitor, suramin, thrombospondin, antibodies directed against proangiogenic factors (for example, Avastin, Erbitux, Vectibix, Herceptin); low molecular weight tyrosine kinase inhibitors of proangiogenic growth factors (for example Tarceva, Nexavar, Sutent, Iressa); mTOR inhibitors (for example Torisel); interferon alpha, beta. and gamma, IL-12, matrix metalloproteinase inhibitors (for example, COL3, marimastat, batimastat); ZD6474, SU11248, vitaxin; PDGFR inhibitors (for example Gleevec); NM3 and 2-ME2; cyclopeptides such as cilengitide.

"Ant metastatic agent" is understood as a chemical or biological substance which. inhibits or reduces metastasis, i.e., the distance propagation, fundamentally by the lymphatic or blood stream, of the cancer causing cells, and the growth of new tumors in the destination sites of said metastasis.

Antimetastatic agents that can be conjugated with the antibodies of the invention include, without limitation, any cytotoxic agent capable of acting as an antimetastatic agent, such as alkylating agents; antimetabolites such as 5-fluorouracil, permetrexed (MTA), raltitrexed (TDX); platinum cytotoxic agents such as cisplatin or oxaliplatin; topoisomerase inhibitors; antimicrotubule agents; anthracyclines; plant alkaloids; GTPase inhibitors; angiogenesis inhibitors; matrix metalloproteinase inhibitors; inhibitors of the cell cycle regulating kinases, such as the cyclin-dependent kinases and cyclin inhibitors; Writ signaling inhibitors; inhibitors of the E2F transcription factor; histone deacetylase inhibitors; AKT kinase or ATPase inhibitors.

The conjugates of the antibody and other agents can be created using a variety of coupling agents or bifunctional protein linkers. The linker can be a "cleavablee linker" which allows the release of the agent in the cell, such as an acid-labile linker, a peptidase-sensitive linker, a dimethyl linker or a linker containing disulphide.

Thus, in another aspect, the invention relates to conjugates comprising a specific anti-S100P monoclonal antibody produced by a hybridoma selected from the group of ECACC 10121601, ECACC 10121602, ECACC 10121603 and ECACC 10121604 or a polypeptide having at least one fragment of the sequence of said monoclonal antibody with capacity for binding to S100P for use in medicine.

In another aspect, the invention relates to the use of a conjugate comprising a specific anti-S100P monoclonal antibody produced by a hybridoma selected from the group of ECACC 10121601, ECACC 10121602, ECACC 10121603 and ECACC 10121604 or a polypeptide having at least one fragment of the sequence of said monoclonal antibody with capacity for binding to S100P for the preparation of a medicament for the prevention and/or treatment of cancer.

In another aspect, the invention relates to a conjugate comprising a specific anti-S100P monoclonal antibody produced by a hybridoma selected from the group of ECACC 10121601, ECACC 10121602, ECACC 10121603 and ECACC 10121604 or a polypeptide having at least one fragment of the sequence of said monoclonal antibody with capacity for binding to S100P for its use in the preparation of a medicament for the prevention and/or treatment of cancer.

In another aspect, the invention relates to a method of treatment or prevention in an individual suffering from cancer which comprises administering to said subject a conjugate comprising a specific anti-S100P monoclonal antibody produced by a hybridoma selected from the group of ECACC 10121601, ECACC 10121602, ECACC 10121603 and ECACC 10121604 or a polypeptide having at least one fragment of the sequence of said monoclonal antibody with capacity for binding to S100P.

"Medicament", in the context of these inventive aspects, is understood as a pharmaceutical composition comprising a conjugate of a monoclonal antibody of the invention or a polypeptide having at least one fragment of the sequence of said monoclonal antibody with a compound useful in the treatment of cancer.

The terms "prevention", "treatment" and "cancer" have been previously defined in the context of the therapeutic uses of the invention.

Diagnostic Method of the Invention

Since the S100P protein is secreted into the extracellular medium by the tumor cells, its presence can be detected in various biofluids, it being able to be used for diagnosing cancer.

Therefore, another aspect of the invention is related to an in vitro method for diagnosing cancer in a subject which comprises:
 (a) detecting the levels of the S100P protein or of a variant thereof in a biofluid of said subject
 (b) comparing said levels with a reference value
wherein the increased levels of the S100P protein or of a variant thereof with respect to the reference value are indicative of the subject suffering from cancer.

In the context of the present invention, "in vitro method for diagnosing cancer" is understood as a method which allows showing the existence of a malignant tumor in a subject by means of detecting the presence of the S100P protein soluble in a biofluid isolated from the patient. It is also useful for documenting the expression of S100P produced by a tumor prior to administering S100P selecting drugs to allow a suitable selection of patients and the determination of the optimal dose.

"Subject" in the present invention is understood as any animal classified as mammal and includes but is not limited to domestic and farm animals, primates and humans, for example human beings, non-human primates, cows, horses, pigs, sheep, goats, dogs, cats or rodents. Preferably, the subject is a female or male human being of any race or age. In the context of the present invention, the subject is a subject who potentially suffers from cancer or has been previously diagnosed with cancer.

The first step of the method of the invention comprises determining the levels of the S100P protein or of a variant thereof in a biofluid of the study subject.

The term "biofluid" in the context of the present invention refers to any biological secretion or fluid, whether physiological or pathological, which is produced in the body of a subject. Such biofluids include, without limitation, blood, plasma, serum, bronchoalveolar washing fluid, urine, nasal secretion, ear secretion, urethral secretion, cerebrospinal fluid, pleural fluid, synovial fluid, peritoneal fluid, ascites fluid, pericardial liquid, amniotic fluid, gastric juice, lymphatic fluid, interstitial fluid, saliva, sputum, liquid deposition, tears, mucus, sweat, milk, semen, vaginal secretions, fluid coming from ulcer, blisters, abscesses and other surface eruptions. Said samples can be obtained by conventional methods, using processes known in the state of art by the person skilled in the art, such as blood extraction, instillation and aspiration of liquid during bronchofibroscopy, cisternal, ventricular or lumbar puncture, pleural puncture or thoracocentesis, joint or synovial percutaneous puncture, abdominal puncture, amniocentesis, expectoration, peritoneal percutaneous puncture, pericardial percutaneous puncture, etc., or by simple harvesting.

In a preferred embodiment, the biofluid is selected from blood, plasma and serum, preferably serum, more preferably plasma. The blood sample is typically extracted by means of puncturing an artery or vein, normally a vein from the inner part of the elbow or from the back of the hand, the blood sample being collected in a air-tight vial or syringe. A capillary puncture normally on the heel or on the distal phalanxes of fingers can be performed for analysis by means of a micromethod. Serum can be obtained from the complete blood sample and in the absence of anticoagulant by leaving the sample to settle for 10 minutes so that it coagulates and subsequently centrifuging it at 1,500 rpm for 10 minutes for the purpose of separating the cells (precipitate) from the serum (supernatant). In turn, to obtain the plasma sample the complete blood is contacted with an anticoagulant and is centrifuged at 3,000 rpm for 20 minutes. The precipitate of said centrifugation corresponds to the formed elements, and the supernatant corresponds to the plasma.

The serum or the plasma obtained can be transferred to a storage tube for sample analysis by means of the method of the invention.

The levels of expression of the S100P protein can be detected and quantified by means of conventional methods. Said methods include, without limitation, the detection of S100P by measuring its affinity to one of its ligands such as RAGE, and the subsequent quantification of the S100P-ligand complex; or by means of using antibodies with capacity of binding specifically to the S100P protein (or fragments thereof which contain the antigenic determinants) and the subsequent quantification of the resulting antigen-antibody complexes. In a preferred embodiment of the invention, the detection is carried out by means of using an antibody that binds specifically to the S100P protein or of a fragment thereof with capacity for binding to the antigen.

Antibodies that can be used in these assays are, for example, serum polyclonal antibodies; supernatants of hybridomas or monoclonal antibodies; chimeric antibodies; humanized antibodies; primatized antibodies; human antibodies; bispecific antibodies; and antibody fragments such as Fab, Fab', F(ab')$_2$, scFv, diabodies, triabodies, tetrabodies and nanobodies. All of the above have been previously described in the context of the therapeutic uses of the anti-S100P antibodies.

In a particular embodiment, the antibody used in the method of the invention is a monoclonal antibody produced by a hybridoma selected from the group consisting of ECACC 10121601, ECACC 10121602, ECACC 10121603 and ECACC 10121604 or a functional variant of said antibody, as described in the context of the second aspect of the invention.

In addition, the antibodies used in the method of the invention may or may not be labeled with a detectable agent. In a particular embodiment the antibody used is conjugated to a detectable agent.

In the context of the present invention, the terms "detectable agent" and "labeling" are synonyms and they refer to an agent the nature of which allows its detection by means of enzymatic, radioactive or fluorescence methods. The detectable compound can be an enzyme, a radioactively labeled compound or a radioactive isotope, a fluorochrome, a chemiluminescent reagent, an enzymatic substrate or cofactor, an enzymatic inhibitor, a particle, a dye, etc.

The compounds radioactively labeled by means of radioactive isotopes, also called radioisotopes or radionuclides, may include, without limitation, $^{3}H$, $^{14}C$, $^{15}N$, $^{35}S$, $^{90}Y$, $^{99}Tc$, $^{111}In$, $^{125}I$, $^{131}I$. The fluorescent labels may include, without limitation, rhodamine, phosphorus-lanthanides or FITC. The enzymatic labels may include, without limitation, horseradish peroxidase, β-galactosidase, luciferase or alkaline phosphatase. The preferred labeling include, but are not limited to, fluorescein, a phosphatase such as alkaline phosphatase, biotin, avidin, a peroxidase such as horseradish peroxidase and compounds related to biotin or compounds related to avidin (for example, streptavidin or ImmunoPure® NeutrAvidin available from Pierce, Rockford, Ill.).

There is a wide variety of well known assays which can be used in the present invention, these assays use primary non-labeled antibodies and secondary labeled antibodies: such techniques include Western-blot or Western transfer, ELISA (Enzyme Linked Immunosorbent Assay), RIA (radioimmunoassay), competitive EIA (competitive enzyme immunoassay), DAS-ELISA (double antibody sandwich ELISA), or techniques based on the use of protein microarrays or biochips which include specific antibodies or assays based on the colloidal precipitation in forms such as reactive strips. Other ways for detecting the S100P protein include techniques such as affinity chromatography, ligand binding assays, etc. There are commercial antibodies against the S100P protein in the market which can be used in the context of the present invention.

In a particular embodiment, the quantification of the levels of S100P is performed by means of Western-blot or ELISA.

In yet a more particular embodiment, the levels of the S100P protein or of its variants are determined by Western-blot. Western-blot is based on detecting the previously resolved proteins by means of electrophoresis in gel under denaturing conditions and being immobilized on a membrane, generally nitrocellulose, by means of incubation with a antibody specific for S100P and a development system (e.g. chemiluminescent).

In another preferred embodiment, the diagnostic is performed by means of ELISA. Said technique is based on the detection of the S100P protein in a sample by means of an anti-S100P antibody immobilized on a substrate and the subsequent detection of the S100P-antibody complex by means of a second antibody. Commercial kits for carrying out the diagnostic such as S100P (Human) ELISA kit from Abnova (Cat. No. KA0093) can be used.

The term "protein" as used herein refers to a molecular chain of amino acids, joined by covalent or non-covalent bonds. The term further includes all the physiologically relevant post-translational chemical modification forms. Post-translational modifications which fall within the scope of the present invention include, for example, signal peptide cleavage, glycosylation, acetylation, phosphorylation, isoprenylation, proteolysis, myristoylation, protein folding and proteolytic process, etc. Additionally, the proteins can include non-natural amino acids formed by post-translational modifications or by means of introducing non-natural amino acids during translation.

The term "S100P" has been defined in the context of the first inventive aspect of the invention. For the diagnostic method of the invention, the detected S100P is that which corresponds to the species to which the subject from which the biofluid sample to be analyzed has been extracted belongs.

As mentioned above, variants of said protein can also be used to measure the levels of the S100P protein in the method of the invention.

Therefore, variants of the S100P protein can be: (i) those in which one or more of the amino acid residues are substituted by a conserved or non-conserved amino acid residue (preferably a conserved amino acid) and such substituted amino acid residue may or may not be encoded by the genetic code, (ii) those in which there are one or more modified amino acid residues, e.g. residues that are modified by the coupling of substituting groups, (iii) those in which the protein is an alternative splicing variant of the S100P and/or (iv) fragments of the protein. The fragments include proteins generated through proteolytic process (including proteolysis at multiple sites) of an original sequence. Said variants fall within the scope of the present invention.

Variants according to the present invention include amino acid sequences that are at least 60%, 70%, 80%, 90%, 95% or 96% similar or identical to the original amino acid sequence. As it is known, the "similarity" between two proteins is determined by means of comparing the amino acid sequence of a protein with a sequence of a second protein. The degree of identity between two proteins is determined using computer algorithms and methods that are widely known by the person skilled in the art, preferably using the BLASTP algorithm [BLASTManual, Altschul, S., et. al., NCBI NLM NIH Bethesda, Md. 20894, Altschul, S., et. al., J. Mol. Biol. 215: 403-410 (1990)].

In a particular embodiment, the variant is a variant from mammal, preferably a human variant, more preferably with at least 60%, 70%, 80%, 90%, 95% or 96% similarity or identity with the original amino acid sequence.

The person skilled in the art will appreciate that the method of the invention can be put into practice using both the absolute level and the relative level of expression of the S100P protein. Thus, in the present invention, the expression "levels of the S100P protein" is used to refer both the absolute levels and the relative levels of said protein.

The expression "absolute levels" refers to the total amount of the protein of interest in a sample. Said value may be given as the concentration of protein expressed in units of mass per unit of volume (e.g. in ng/ml of sample), in the number of protein molecules per unit of volume (e.g. in pmol protein/ml of sample), in the units of mass of S100P protein per unit of mass of total protein (pg S100P/mg total protein) or in the number of S100P molecules per unit of mass of total protein (e.g. in pmol S100P/mg of total protein).

The expression "relative levels" refers to the relationship between the levels of expression of the S100P protein object of the study and of a reference protein, i.e., the concentration of S100P protein in normalized form with respect to said reference protein is defined.

In order to normalize the values of protein between the different samples, it is possible to compare the levels of S100P protein in the samples to be analyzed with the expression of a control protein. "Control protein" in the present invention is understood as a protein the levels of expression of which do not change or only change in limited amounts in the tumor cells with respect to the non-tumor cells. Preferably, the control protein is a protein encoded by genes that are constitutively expressed, s that are those genes always active or being transcribed constantly, such that these proteins are constitutively expressed and carry out essential cellular functions. Preferred control proteins that can be used in the present invention include, without limitation, β-2-microglobulin (B2M), ubiquitin, 18-S ribosomal protein, cyclophilin, GAPDH, PSMB4, tubulin and actin. In a more preferred embodiment the control protein is tubulin.

The person skilled in the art understands that mutations in the amino acid sequence of the S100P protein do not affect the detection of the expression thereof and, therefore, the variants of this protein generated by mutations of the amino acid sequence fall within the scope of the present invention.

Once the level of expression of S100P in a sample has been determined, step (b) of the invention which consists of comparing the levels of S100P obtained in step (a) with a reference value takes place.

The "reference value" derives from a sample collection formed preferably by a mixture of the biofluid to be analyzed from normal individuals not affected by cancer. Said reference value can be determined by means of techniques well known in the state of the art, for example, determining the mean of the levels of S100P protein measured in biofluids taken from healthy subjects. The reference value can also be obtained from the constitutively expressed proteins taken from the same subject to be analyzed.

Once the reference value is established, the value of the levels of S100P obtained in step (a) can be compared with this reference value and, therefore, allows detecting alterations in the levels of S100P protein of the subject with respect to the reference value. More specifically, in the method of the invention, an increase of the levels of S100P with respect to the reference value is indicative of the subject suffering from cancer.

In the context of the present invention, "increased levels" with respect to the reference value is understood as a variation of the levels of S100P above the reference value of at least 1.1 times, 1.5 times, 5 times, 10 times, 20 times, 30 times, 40 times, 50 times, 60 times, 70 times, 80 times, 90 times, 100 times or even more times as compared to the reference value.

Therefore, once said comparison has been performed, the method of the invention allows diagnosing if the subject suffers from cancer. In a particular embodiment, the method is suitable for diagnosing any cancer with the exception of colon and pancreatic cancer, preferably with the exception of colon cancer, more preferably with exception of pancreatic cancer. In another particular embodiment, the cancer that is diagnosed is a pancreatic cancer, preferably pancreatic adenocarcinoma.

Kits of the Invention and Uses Thereof

In another aspect, the invention relates to a kit for diagnosing cancer in a biofluid which comprises at least one antibody according to the second aspect of the invention, i.e., one specific anti-S100P monoclonal antibody produced by a hybridoma selected from the group of ECACC 10121601, ECACC 10121602, ECACC 10121603 and ECACC 10121604 or a polypeptide having at least one fragment of the sequence of said monoclonal antibody with capacity for binding to S100P. In a particular embodiment, the cancer is any cancer with the exception of colon and pancreatic cancer, preferably with the exception of colon cancer, more preferably with the exception of pancreatic cancer. In another particular embodiment, the cancer is a pancreatic cancer, preferably pancreatic adenocarcinoma.

In another aspect, the invention relates to the use of a kit as previously defined for diagnosing cancer in the biofluid of a subject. In a particular embodiment, the cancer is any cancer with the exception of colon and pancreatic cancer, preferably with the exception of colon cancer, more preferably with the exception of pancreatic cancer. In another particular embodiment, the cancer is a pancreatic cancer, preferably pancreatic adenocarcinoma.

The term "kit", as used in the present document, refers to a combination of a set of reagents suitable for detecting the levels of S100P together with one or more types of elements or components (for example, other types of biochemical reagents, containers, packaging suitable for its commercial sale, substrates to which the reagents are bound, electronic hardware components, etc.)

In the present invention, "reagent suitable for detecting the levels of S100P" is understood as a specific anti-S100P monoclonal antibody produced by a hybridoma selected from the group of ECACC 10121601, ECACC 10121602, ECACC 10121603 and ECACC 10121604 or a polypeptide having at least one fragment of the sequence of said monoclonal antibody with capacity for binding to S100P and, optionally, reagents for detecting one or more constitutive proteins.

As it will be understood by the person skilled in the art, the antibodies of the kit of the invention can be used in all the techniques for determining the levels of protein known to be suitable for the analysis of a biofluid, such as Westernblot or Western transfer, ELISA, RIA, competitive EIA, DAS-ELISA, techniques based on the use of biochips, protein microarrays, assays of colloidal precipitation in reactive strips, etc.

The antibodies can be fixed to a solid support such as a membrane, a plastic or a glass, optionally treated to facilitate the fixation of said antibodies to the support. Said solid support comprises, at least, a set of antibodies which specifically recognize the S100P protein, and which can be used for detecting the levels of expression of said protein.

The kits of the invention additionally comprise reagents for detecting a protein encoded by a constitutive gene. The availability of said additional reagents allows normalizing the measurements performed in different samples (for example, the sample to be analyzed and the control sample) to rule out that the differences in the expression of the biomarkers are due to a different quantity of total protein amount in the sample more than the real differences in the relative levels of expression. The constitutive genes in the present invention are genes that are always active or being transcribed constantly and which encode for proteins that are expressed constitutively and carry out essential cellular functions. Proteins that are expressed constitutively and can be used in the present invention include, without limitation, β-2-microglobulin (B2M), ubiquitin, 18-S ribosomal protein, cyclophilin, GAPDH, PSMB4, tubulin and actin.

All the particular embodiments of the method of the present invention are applicable to the kits of the invention and to their uses.

Other Aspects of the Monoclonal Antibodies of the Invention

The monoclonal antibodies of the second aspect of the invention produced by a hybridoma selected from the group of ECACC 10121601, ECACC 10121602, ECACC 10121603 and ECACC 10121604 or a polypeptide having at least one fragment of the sequence of said monoclonal antibody with capacity for binding to S100P can also be useful for detecting S100P in biological samples of another type different from a biofluid. Said detection processes are advantageously applied for the diagnosis and/or prognosis of cancer the tumor cells of which are cells which express the S100P protein.

These monoclonal antibodies can be used for identifying cells and tissues which express the S100P protein by means of standard techniques such as immunofluorescence, flow cytometry, affinity chromatography or immunoprecipitation. For example, a monoclonal antibody of the invention can facilitate the identification of a tumor cell which expresses an S100P protein and allows diagnosing cancer in a subject.

Thus, in another aspect, the invention relates to an in vitro method for diagnosing cancer in a subject which comprises:
  (a) detecting the levels of the S100P protein or of a variant thereof in a cell or tissue of said subject by means of a specific anti-S100P monoclonal antibody produced by a hybridoma selected from the group of ECACC 10121601, ECACC 10121602, ECACC 10121603 and ECACC 10121604 or a polypeptide having at least one fragment of the sequence of said monoclonal antibody with capacity for binding to S100P.
  (b) comparing said levels with a reference value wherein increased levels of the S100P protein or of a variant thereof with respect to the reference value are indicative of the subject suffering from cancer.

The term "in vitro method" implies that said method is carried out in a biological sample isolated from the subject from whom it is taken. Said biological sample can be a cell, such as a blood cell, an epithelial cell, a germ cell, etc. or also a biopsy sample of a tissue.

The terms "levels of the S100P protein", "variant", "reference value" and "increased levels" have already been defined in the context of the method of the invention.

The detection can be facilitated by means of the coupling (i.e., physical binding) of the antibody to a labeling group.

Given that the monoclonal antibodies of the invention recognize the S100P protein, they can be used for purifying said protein from a sample.

Preferably, for use in the purification of S100P, the monoclonal antibodies of the second aspect of the invention are used by associating them with a support or substrate. In principle, any type of support can be used in the methods of the invention, although the use of polymeric type supports such as Sephadex, dextran, polyamino acids soluble in water, polyethylene glycol (PEG), polyglutamic acid (PGA), polylactic acid (PLA), polylactic-co-glycolic acid (PLGA), poly(D,L-lactide-co-glycolide) (PLA/PLGA), poly(hydroxyalkylmethacrylamide), a polyglycerol, a polyamidoamine (PAMAM) and a polyethyleneimine (PEI) is preferable.

Typically, the purification of S100P using the monoclonal antibodies of the second aspect of the invention is carried out by means of a process which comprises the steps of:

(i) contacting the sample from which the S100P protein is to be purified with an antibody produced by a hybridoma selected from the group of ECACC 10121601, ECACC 10121602, ECACC 10121603 and ECACC 10121604 or a polypeptide having at least one fragment of the sequence of said monoclonal antibody with capacity for binding to S100P immobilized on a support in conditions suitable for the binding between the antibody and the S100P protein to take place;

(ii) washing the complexes formed in step (i) to remove all those compounds from the sample that are nonspecifically bound to the support-antibody conjugate and (iii) eluting the S100P protein that is bound to the compound.

The method for purifying the S100P protein of the invention can be carried out using any known protein purification method by means of affinity, including, for example, affinity chromatography columns the stationary phase of which is formed by the monoclonal antibodies according to the second aspect of the invention conjugated to a solid support.

Briefly, the present invention is aimed at:

[1]. Use of an antibody that binds specifically to the S100P protein or of a fragment thereof with capacity for binding to the antigen for the preparation of a medicament for the prevention and/or treatment of cancer.

[2]. Use according to [1] wherein the cancer is a cancer resistant to chemotherapy treatment.

[3]. Use according to [1] or [2] wherein the cancer is pancreatic adenocarcinoma.

[4]. Use according to [1], [2] or [3] wherein the antibody is a monoclonal antibody produced by a hybridoma selected from the group consisting of ECACC 10121601, ECACC 10121602, ECACC 10121603 and ECACC 10121604 or a functional variant of said antibody.

[5]. Specific anti-S100P monoclonal antibody produced by a hybridoma selected from the group of ECACC 10121601, ECACC 10121602, ECACC 10121603 and ECACC 10121604 or a polypeptide having at least one fragment of the sequence of said monoclonal antibody with capacity for binding to S100P.

[6]. Monoclonal antibody or polypeptide according to [5] which is capable of stopping the growth of tumor cells.

[7]. Hybridoma cell line selected from those cell lines deposited with accession number ECACC 10121601, ECACC 10121602, ECACC 10121603 and ECACC 10121604.

[8]. A conjugate comprising a monoclonal antibody or polypeptide according to [5] and a second component selected from the group of:
  (a) a cytotoxic agent
  (b) an antiangiogenic agent
  (c) an antimetastatic agent

[9]. Method for obtaining a monoclonal antibody according to [5] which comprises culturing a hybridoma cell line selected from those cell lines deposited with accession number ECACC 10121601, ECACC 10121602, ECACC 10121603 and ECACC 10121604 in conditions which allow the production of said antibody.

[10]. Pharmaceutical composition comprising a pharmaceutically effective amount of at least one monoclonal antibody or one polypeptide according to [5] and at least one pharmaceutically acceptable excipient.

[11]. Use of a conjugate according to [8] for the preparation of a medicament for the prevention and/or treatment of cancer.

[12]. In vitro method for diagnosing cancer in a subject which comprises:
  (a) detecting the levels of the S100P protein or of a variant thereof in a biofluid of said subject
  (b) comparing said levels with a reference value
wherein increased levels of the S100P protein or of a variant thereof with respect to the reference value are indicative of the subject suffering from cancer.

[13]. Method according to [12] wherein the detection is carried out by means of using an antibody that binds specifically to the S100P protein or of a fragment thereof with capacity for binding to the antigen.

[14]. Method according to [13] wherein the detection is carried out by means of an antibody conjugated to a detectable agent.

[15]. Method according to [13] or [14] wherein the antibody is a monoclonal antibody produced by a hybridoma selected from the group consisting of ECACC 10121601, ECACC 10121602, ECACC 10121603 and ECACC 10121604 or a functional variant of said antibody.

[16]. Method according to [12] to [15] wherein the biofluid is selected from blood, plasma and serum.

[17]. Method according to [16] wherein the biofluid is plasma.

[18]. Method according to [12] to [17] wherein the subject is a human.

[19]. Kit for diagnosing cancer in a biofluid which comprises at least one antibody or one polypeptide according to [5].

The invention is described below by means of the following examples which must be considered as merely illustrative and in no case limiting to the scope of the present invention.

EXAMPLES

The following abbreviations are used in experimental part:
FCS: fetal calf serum
DMEM: Dulbecco's Modified Eagle's culture medium
RPMI: Roswell Park Memorial Institute culture medium
RT-PCR: reverse transcriptase-polymerase chain reaction
SDS: sodium dodecyl sulfate
ELISA: enzyme-linked immunosorbent assay
PBS: phosphate buffered saline
PEG: polyethylene glycol
HAT: hypoxanthine-aminopterin-thymidine
HRP: horseradish peroxidase
TMB: 3,3',5,5'-tetramethylbenzidine
NMWL: nominal molecular weight limit
IGEPAL: octyl phenol ethoxylate
EDTA: ethylenediaminetetraacetic acid
PMSF: phenylmethylsulfonyl fluoride
Tris: tris(hydroxymethyl)aminomethane
PVDF: polyvinylidene fluoride
TBS: Tris buffered saline
Amino acids
Leu: leucine
Val: valine
Pro: proline
Arg: arginine
Gly: glycine
Ser: serine
His: histidine
Preparation of the Human Recombinant S100P Protein and the Monoclonal Antibodies Example 1: Origin and Preparation of the Cultures and the Tumor Cell Lines The pancreatic adenocarcinoma cell line BxPC3 (ECACC, No.: 93120816) was cultured in RPMI 1640 with L-Glutamine (Sigma) supplemented with 10% FCS (Invitrogen).

The cervical epithelioid carcinoma cell line HeLa (ECACC, No.: 93021013) was cultured in DMEM/F12 with L-Glutamine (Sigma) supplemented with 10% FCS (Invitrogen).

The myeloma cells were cultured in RPMI 1640 with L-Glutamine (Sigma) supplemented with 10% FCS (PAA; Australian origin).

All the cells were cultured at 37° C. in an incubator with 5% $CO_2$ in a humidified atmosphere. All the cultures tested with the Venor® GeM (Minerva Biolabs) mycoplasma test kit were negative for mycoplasma.

Example 2: Obtaining the Human Recombinant S100P Protein

A fragment which encoded the complete human S100P sequence was obtained by RT-PCR from the mRNA of the HeLa cell line derived from a human cervical epithelioid carcinoma. The specific primers used in the PCR were:

(SEQ ID NO: 3)
5'-ACTCACATATGACGGAACTAGAGACAGCCATGGGCATGATC-3'

(SEQ ID NO: 4)
5'-ACTCATGAGCTCATCATTTGAGTCCTGCCTTCTCAAA
GTACTT-3'

The cDNA of S100P was cloned into the NdeI site of the bacterial expression vector pET28a (+) (Novagen), and the positive clones were selected and confirmed by sequencing the DNA. This construct was transformed into competent *E. coli* Tuner™ (DE3) (Novagen) cells, and the expression of the protein was induced with 1 mM isopropyl β-D-thiogalactopyranoside (IPTG) (Sigma) for 6 hours. The bacteria were later harvested and lysed by sonication in buffer A (100 mg/ml lysozyme, 0.5 M NaCl, 10 mM $Na_2HPO_4.2H_2O$, 10 mM $NaH_2PO_4.2H_2O$, 10 mM imidazole, pH 7.5). The lysate was cleaned by centrifugation and was filtered through a HiTrap™ chelating affinity column (Amersham). The protein was eluted with buffer B (0.5 M NaCl, 10 mM $Na_2HPO_4.2H_2O$, 10 mM $NaH_2PO_4.2H_2O$ and 300 mM imidazole, pH 7.5). In some experiments, the histidine chain was removed with thrombin protease (Novagen). The recognition sequence is Leu-Val-Pro-Arg-Gly-Ser (SEQ ID NO:5) with a cutting point between Arg and Gly. Therefore, the complete recombinant S100P protein has additional amino acids, Gly-Ser-His, at the N-terminus end. After digestion, the rest of the poly-His chain was removed by HiTrap™ chelating affinity column (Amersham) using the poly-His chain, and the purity of the supernatant which contained the recombinant S100P protein was tested by electrophoresis in 12% polyacrylamide-SDS gel (w/v).

Example 3: Obtaining the Anti-S100P Monoclonal Antibodies

The fusion process for monoclonal antibody, ELISA detection and subcloning were performed by means of standard technologies. The maintenance, expansion and scaling of the cell culture were performed in a humid environment (94% air and 6% $CO_2$) at 37° C.

Five female mice were immunized with human recombinant S100P (SEQ ID NO: 2) according to the following protocol. Fifty micrograms of S100P protein diluted in PBS (137 mM NaCl, 2.8 mM KCl, 8.1 mM $Na_2HPO_4$, 1.5 mM $KH_2PO_4$, pH 7.2) were used as an emulsion with Freund's complete adjuvant (Sigma) for the initial subcutaneous vaccination route, and with Freund's incomplete adjuvant (Sigma) for subsequent subcutaneous injections at days 19 and 35. Ten days after the third injection, a serum sample was taken from each mouse and they were analyzed. On day 51, a new stimulus injection of 25 mg of S100P protein diluted in PBS was given and it was administered intravenously in the mouse with the highest serum titer.

The fusion was carried out four days after the last injection according to the standard procedures (Harlow D and Lane D. Antibodies: A Laboratory Manual. 1988. Cold Spring Harbor Laboratory Press, Cold Spring Harbor. N.Y.). The monoclonal antibodies obtained were derived from a fusion of myeloma cells with the spleen cells of the mouse at a 1/10 ratio, respectively, using PEG-1500 (Roche Diagnostics) as a fusion inductor. The cells were then seeded in 96-well plates in a medium with HAT (Invitrogen) for selecting the hybrids.

The supernatant of the hybridoma was examined by means of ELISA to see its reactivity with the human recombinant S100P. 50 µl of S100P protein (3 mg/ml in PBS) were used for coating the MaxiSorp (NUNC) 96-microwell plates, leaving them over night at 4° C. After washing with PBS and blocking (1% skim milk in PBS, 1 h, 37° C.), 50 µl of the supernatant of the hybridoma culture were added to each well and they were incubated for two hours at 37° C. After washing 5 times at room temperature with calcium and magnesium free PBS-HT (274 mM NaCl, 2.8 mM KCl, 8.1 mM $Na_2HPO_4$, 1.5 mM $KH_2PO_4$, 0.1% Tween-20, pH 7.2), the anti-mouse goat IgG/IgM immunoglobulins conjugated with HRP (Jackson ImmunoResearch) were detected, using 3,3',5,5'-tetramethylbenzidine (TMB) (Sigma) as a substrate.

For cloning, the wells with an optical density greater than three times the background noise were elected. Clones 5D7, 4B12, 3E3 (internal code 3E3-2A2-5H9; ECACC 10121602), 7F1, 9F3, 6F1, 1A5 (internal code 1A5-2G8-2D1; ECACC 10121601), 3F8 (internal code 3F8-1A9-2G8; ECACC 10121604) and 2H8 (internal code 2H8-3A4-2D3; ECACC 10121603) were selected and subcloned by limiting dilution for their functional analysis. Only subclones which grew at 0.1 and 0.01 cells per well were considered suitable for expansion and were adapted to the DMEM/F12 (Sigma) medium, being subsequently frozen.

For large-scale purification, the hybridoma cells were cultured in DMEM/F12 with L-Glutamine with 10% FCS (PAA, of Australian origin) in a culture vial of 175 $cm^2$. When it reached the concentration of $0.8 \times 10^6$ cells/ml (with viability more than 85%), the culture medium was removed and the cells were washed twice with serum-free DMEM/F12 medium. After this point, 50 ml of a medium containing 80% DMEM/F12, 20% CDHybridoma (Invitrogen) and 2 mM of L-Glutamine were added to each vial and they were incubated for 96 hours. Finally, the serum-free medium was collected, centrifuged and frozen until purification.

After the filtration, the purification was performed by means of a 5 ml HiTrap-HP (Amersham) protein G affinity column. The eluted antibodies were concentrated and diafiltered in PBS with Amicon® Ultra-15 devices with ULTRACEL® (30000 NMWL, Millipore) low exclusion membranes. The amount of antibody was finally quantified by measuring the absorbance at 280 nm.

Characterization of the Monoclonal Antibodies Generated

Example 4: Characterizing the Cross-Reactivity of the Anti-S100P Monoclonal Antibodies: 5D7, 4B12, 3E3, 7F1, 9F3, 6F1, 1A5, 3F8 and 2H8 Monoclonal Antibodies Only React with Human S100P The anti-S100P antibodies were tested to determine if there was cross-reaction against other members of the S100 family: the S100A1, S100A2, S100A6 (Abnova) human recombinant proteins; and the S100A7, S100A4 human recombinant proteins (cloned from MDA-MD-468 human breast adenocarcinoma cell line and from HCT116 colon adenocarcinoma line, respectively, in Leitat Biomed Division). The determination of the immunoglobulin isotypes for these antibodies was performed using a mouse immunoglobulin subtyping kit (Sigma).

The selection of antibodies by ELISA for human S100P, human S100A2, human S100A1, human S100A6, human S100A7 and human S100A4 showed that the 5D7, 4B12, 3E3, 7F1, 9F3, 6F1, 1A5, 3F8 and 2H8 monoclonal antibodies showed reactivity only with human S100P (Table 1). The isotype analyses demonstrated that all the antibodies are IgG1.

TABLE 1

Specificity of the antibodies analyzed by ELISA.
Monoclonal antibody reaction pattern by ELISA

| Antibodies | Immunogen | Isotype | Human S100P | Human S100A1 | Human S100A2 | Human S100A6 | Human S100A7 | Human S100A4 |
|---|---|---|---|---|---|---|---|---|
| 5D7, 4B12, 3E3, 7F1, 9F3, 6F1, 1A5, 3F8, 2H8 | Human S100P | IgG1 | ++++ | − | − | − | − | − |

++++ positive reaction,
− negative reaction

Example 5: Characterizing 3F8 Monoclonal Antibody by Western-Blot

All the tested antibodies (5D7, 4B12, 3E3, 7F1, 9F3, 6F1, 1A5, 3F8, 2H8) recognized both the human recombinant S100P protein as well as the natural protein of the cell itself.

The results herein presented show the recognition of the 3F8 antibody, but this can be extendable to the remaining antibodies.

Samples from cell lines were washed twice with PBS and were lysed in cell lysis buffer (150 mM NaCl, 1% IGEPAL CA630, 5 mM EDTA, 100 mg/ml PMSF, 1 mM $Na_3VO_4$, 1 mM NaF and 50 mM TrisHCl, pH 7.4) at 4° C. The lysates were purified by centrifugation and the concentration of protein was quantified with the Bradford reagent (Bio-Rad). The total extracts (50 µg) were resolved in 12% SDS-polyacrylamide gel in reducing conditions and were transferred to PVDF BioTrace™ (Pall Corporation) membranes. The membranes were blocked for 1 hour in TBS plus 0.1% Tween-20 and 5% skim milk powder; they were incubated over night with the corresponding primary antibody and then with the secondary antibodies for 1 hour in blocking buffer. After each incubation, three consecutive 10-minute washes were performed in TBS plus 0.1% Tween-20. The signal was developed using the ECL™ (Amersham) detection reagent exposing the membranes in Hyperfilm™ ECL (Amersham) photographic paper.

The concentrations used for the antibodies were the following: mouse human anti-S100P 3F8 monoclonal antibody (Leitat Biomed Division) at 1 mg/ml; mouse anti-actin-HRP monoclonal antibody (Sigma) at a concentration of 0.15 µg/ml; and anti-mouse goat IgG polyclonal antibody (Jackson ImmunoResearch) at 0.04 mg/ml as the secondary antibody.

FIG. 1 shows the expression pattern of the S100P protein in several tumor cell lines. The pancreatic adenocarcinoma BxPC3, colon adenocarcinoma HT29 and colo205, and breast adenocarcinoma MDA-MB-468 and MCF7 tumor lines showed the highest expression levels of S100P. The PC3 (prostate adenocarcinoma) and MDA-MB-231 (breast adenocarcinoma) lines also showed expression Pharmacological Activities of the Anti-S100P Monoclonal Antibodies Example 6: S100P Induces the Proliferation of BxPC3 Tumor Cells and the Anti-S100P Monoclonal Antibodies Block this Activity The proliferation studies on the BxPC3 line were analyzed using the Cell Proliferation ELISA Biotrak™ System kit (GE Healthcare) following the manufacturer's instructions with some modifications. Three thousand cells were seeded in 50 µl of RPMI 1640 culture medium supplemented with 3% FCS in each well. The recombinant S100P protein (100 nM) alone or in combination with the antibodies was added to the cells in the same seeding medium to test the proliferative or inhibitory capacity thereof, respectively. To test the inhibitory effect of the 5D7, 4B12, 3E3, 7F1, 9F3, 6F1, 1A5, 3F8 and 2H8 monoclonal antibodies, a concentration of 500 nM of each antibody was incubated for 2 hours at 37° C. with the recombinant S100P protein before being added to the culture. After 48 hours at 37° C., the proliferation was determined. The two-tailed Mann-Whitney nonparametric test was used to compare the groups. A p value <0.05 was taken for the values to be statistically significant.

This experiment demonstrated for the first time that the combination of S100P with an antibody directed against it inhibited in a statistically significant manner the proliferation induced by the protein on a BxPC3 pancreatic adenocarcinoma tumor cell culture.

Figure 2:
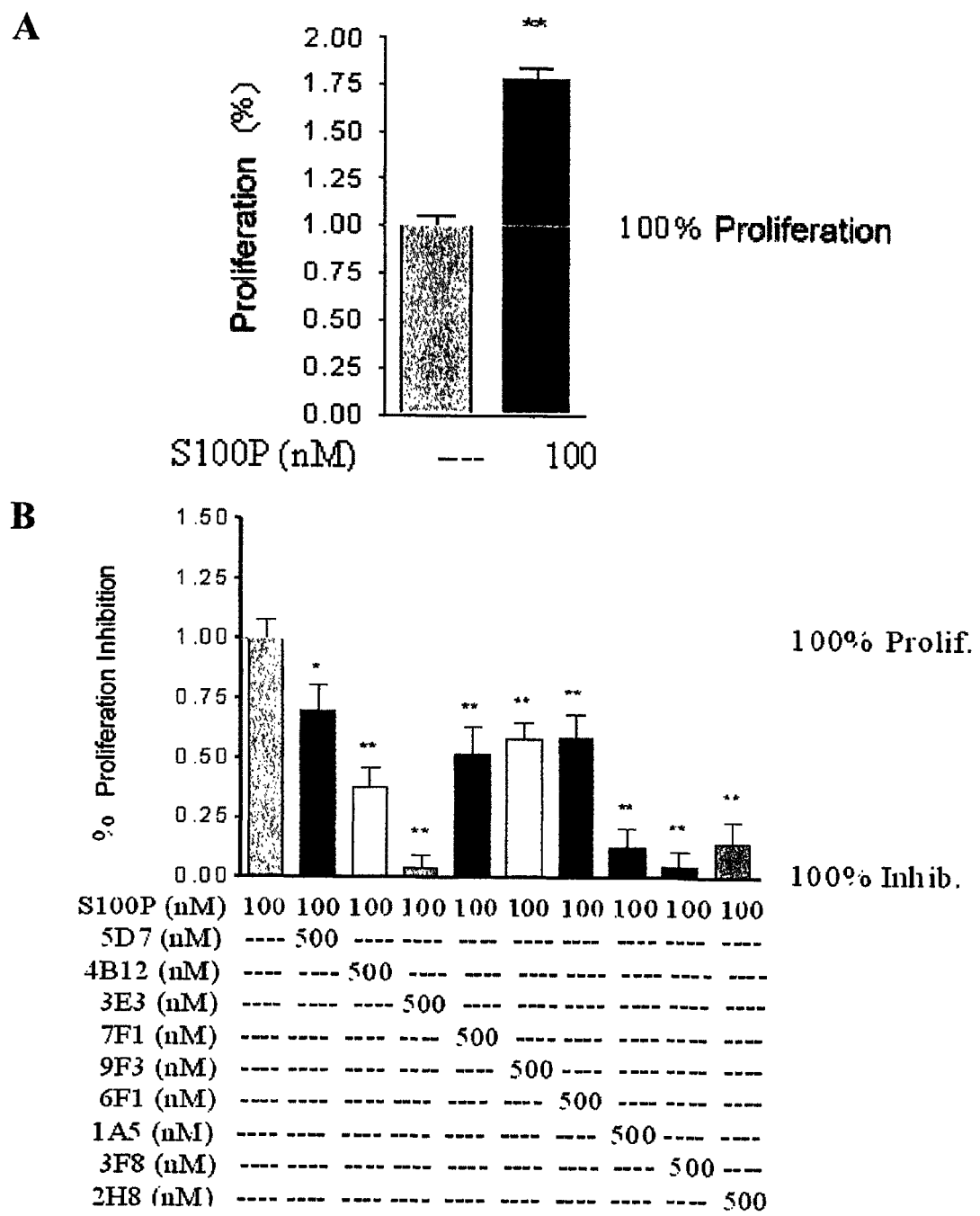
FIG. 2 shows the neutralizing effect of anti-S100P monoclonal antibodies on the proliferation induced by the S100P protein in the BxPC3 pancreas tumor line. A) Increase of proliferation induced by the human recombinant S100P protein (100 nM) in the BxPC3 line. Each piece of data is normalized in relation to the basal proliferation of the cells without S100P, which represents 100% proliferation. The bars show the average±standard deviation. **$p<0.005$ (non-parametric Mann-Whitney U test). B) Inhibiting effect of several antibodies of the invention directed against the S100P protein. The cells were treated with S100P (100 nM) or the combination of this protein with the antibodies (500 nM) for 48 hours. Each piece of data is normalized in relation to the proliferation induced by S100P (left bar), which represents 100% proliferation. The bars show the average±standard deviation. *$p<0.05$**$p<0.005$ (non-parametric Mann-Whitney U test). Prolif.: proliferation; Inhib.: inhibition. The anti-S100P monoclonal antibodies from the hybridomas 1A5-2G8-2D1 (ECACC 10121601), 3E3-2A2-5H9 (ECACC 10121602), 2H8-3A4-2D3 (ECACC 10121603) and 3F8-1A9-2G8 (ECACC 10121604) are indicated by means of their abbreviated name 1A5, 3E3, 2H8 and 3F8, respectively.

As can be observed in FIG. 2A, the S100P protein induces a proliferation increase of virtually 80% compared to the cells not treated with said protein.

The anti-S100P monoclonal antibodies (5D7, 4B12, 3E3, 7F1, 9F3, 6F1, 1A5, 3F8, 2H8) were also used to block the proliferative activity of S100P. As is shown in FIG. 2B, 500 nM of the 3E3, 1A5, 3F8 and 2H8 antibodies almost completely abolished the effect of S100P (96.2%, 87.7%, 95.7% and 86.1% of inhibition, respectively), whereas the rest had lower but also statistically significant activities. Overall, these results demonstrate that antibodies designed against the human S100P protein neutralize the proliferative capacity of the latter on cell growth.

Example 7: Origin and Preparation of Animals

Mice for antibody production (female BALB/cAnNHsd; 6 weeks old) and for tumor models ("nude mice": female athymic (Hsd:Athymic Nude-Foxnlnu; 6-7 weeks old) were from Harlan Laboratories Models, S.L. (Barcelona, Spain). Nude mice were maintained in sterile room in micro-isolator cages, and were given sterilized food and water ad libitum. All manipulations were performed in a laminar flow hood.

Example 8: 3F8 and 2H8 Block BxPC3 Tumor Progression in Nude Mice

The antitumorigenic and antimetastatic capability of the monoclonal antibodies 3F8 and 2H8 against S100P was assessed in an orthotopic tumor model using the human adenopancreatic BxPC3 tumor cell line stably expressing a lentiviral luciferase reporter gene.

BxPC3-luc cell line in exponential growth were harvested with trypsin-EDTA (0.05%/0.02%) (Invitrogen), washed, and examined for viability by trypan blue dye exclusion. Viability was greater than 95%. For primary tumor growth, cells (5×105 in 0.1 mL DMEM high glucose) were injected into the pancreas of 5 nude mice.

Four weeks after cell injection, when tumors became established (300-350 mm3), two animals were killed, tumors were obtained, sliced in 5 mm3 pieces approximately and implanted in 15 new mice. Mice were divided into 3 groups of five animals each one.

Tumor growth and metastasis were followed by bioluminescent imaging, palpation of animals and the examination of endpoint criteria of treated animals (occurrence of ascitic fluid and body weight loss).

Mice were treated either with cromolyn (reference compound that is known to bind to S100P and block its extracellular activity, Arumugam T. et al. 2006. J. Natl. Cancer Inst. 98(24):1806-18), daily (5 mg/Kg body weight by ip injection) or with our antibodies against S100P (3F8 and 2H8), three times per week at 25 mg/Kg by ip injection, starting the treatment 24 hours after tumor implantation. At the end of the experiment (treatment of 30 days) animals were killed, pancreatic tumors were surgically removed, weighted and an staging and scoring system of peritoneal tumors, pancreatic tumors, lymph node metastases, organ metastases, and ascites was developed and recorded according to our TMPN scoring system (Table 2) modified from Hennig R. et al. 2005. Neoplasia, 7(4):417-425 to evaluate tumor progression. Scores from each category were multiplied with each other because patterns in medicine follow multiplicative, rather than additive, rules.

TABLE 2

TMPN Classification and Scoring System
Staging and Scoring System

| Stage | Description | Score |
|---|---|---|
| Primary Tumor | | |
| $T_0$ | No tumor | 1 |
| $T_1$ | Small tumor (tumor d < 7 mm) | 2 |
| $T_2$ | Large tumor without infiltration (tumor d > 7 mm) | 3 |
| $T_3$ | Large tumor with infiltration but still visible margins | 4 |
| $T_4$ | Diffuse and infiltrating tumor | 5 |
| Organ Metastases | | |
| $M_0$ | No liver or lung metastases | 1 |
| $M_{1Li}$ | Liver metastases | 5 |
| $M_{1Lu}$ | Lung metastases | 5 |
| $M_1$ | Liver and lung metastases | 10 |
| Peritoneal Metastases | | |
| $P_0$ | No peritoneal metastases | 1 |
| $P_1$ | Less than five peritoneal metastases or one with d < 7 mm | 3 |
| $P_2$ | More than five peritoneal metastases or one with d > 7 mm | 4 |
| $P_3$ | Malignant ascites | 5 |
| $P_4$ | Diaphragm/kidney/intestine/adrenal metastases | $3 + 3 + 3 + 3 + P_{0/1/2/3}$ |
| Lymph Node Metastases | | |
| $N_0$ | No lymph node metastases | 1 |
| $N_1$ | Peripancreatic lymph node metastases | 3 |

TABLE 2-continued

TMPN Classification and Scoring System
Staging and Scoring System

| Stage | Description | Score |
|---|---|---|
| $N_2$ | Regional lymph node metastases (e.g., mesenteric, mediastinal) | 5 |

Scores for the primary tumor (T), organ metastases (M), peritoneal metastases (P), and lymph node metastases (N) were multiplied to calculate the total tumor score for each animal. Score P4 value is the sum of the corresponding $P_0$, $P_1$, $P_2$, $P_3$ ($P_{0/1/2/3}$) plus an additional value of 3 for metastasis presence in the diaphragm, 3 for kidney, 3 for intestine and 3 for adrenal glands.

Bioluminescence imaging was conducted using a cryogenically cooled IVIS 100 imaging system coupled to a data acquisition computer running Living Image Software (Xenogen Corp). Before imaging, mice were placed in an acrylic chamber anesthetized with 2.5% isofluorane-air mixture, and injected intraperitoneally with 15 mg/mL of luciferin potassium salt in PBS at a dose of 150 mg/Kg body weight. At the end of experiment, after the primary tumors were removed, cancer cell dissemination and metastasis were visualized using IVIS imaging, and metastatic colonies were counted and measured (photons/second).

Figure 5:
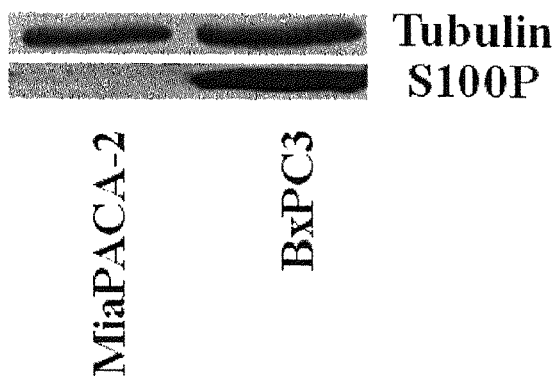
FIG. 5 shows the determination of S100P protein in plasma samples derived from BxPC3 and MiaPACA-2 cell line tumor xenograft models determined by sandwich ELISA. A) Expression of S100P in tumor samples (BxPC3 and MiaPACA-2 cell lines) determined by Western blot. B) Plasma levels of S100P in animals with BxPC3 tumors compared with levels in animals with MiaPACA-2 tumors (null expression of S100P). Plasma levels were measured at the end of the experiment. Graph of plasma levels show the mean±standard deviation. **$p<0.005$ ("Mann-Whitney U test").
Figure 5:
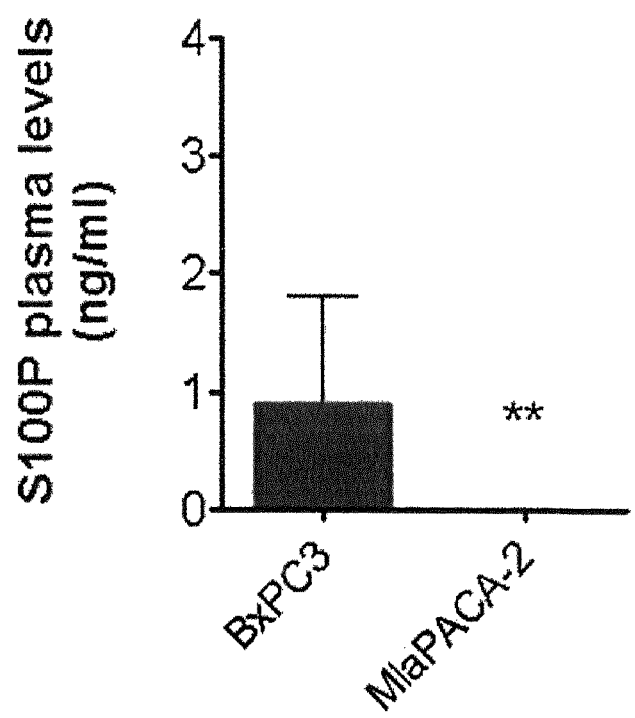

The inventors investigated the effect of the 3F8 and 2H8 monoclonal antibodies on the onthotopic development of BxPC3 tumors, cancer cell dissemination and metastasis formation in athymic nude mice. Either BxPC3 cell line or developed tumors from this line in nude mice show high levels of S100P protein expression and secretion of the protein into the culture media and into the blood, respectively (FIG. 5). Due to the role of S100P in pancreatic tumors and the evidence that the protein is secreted by this cell line, we decided to try this model to test the in vivo activity of our monoclonal antibodies 3F8 and 2H8.

Table 3 shows the comparative analysis of the total score at the end of the experiment for each animal according to the TMPN classification (Table 3).

| | | | Organ Metastases | | Peritoneal Metastases | | | | | | |
|---|---|---|---|---|---|---|---|---|---|---|---|
| | Animal | Tumor | Liver | Lung | Diaphragm | Kidney | Adrenals | Intestine | Peritoneum | Nodes | Total Score |
| G1 (Cromolyn) | 1 | 4 | 5 | 5 | 0 | 3 | 3 | 3 | 4 | 5 | 2600 |
| | 2 | 4 | 5 | 0 | 3 | 0 | 0 | 3 | 4 | 5 | 1000 |
| | 3 | 4 | 5 | 0 | 3 | 3 | 0 | 3 | 4 | 5 | 1300 |
| | 4 | 5 | 5 | 0 | 3 | 3 | 0 | 3 | 5 | 5 | 1750 |
| | 5 | 4 | 5 | 0 | 3 | 0 | 0 | 3 | 4 | 5 | 1000 |
| | 6 | 5 | 5 | 0 | 3 | 3 | 0 | 3 | 5 | 5 | 1750 |
| G2 (mAb 3F8) | 1 | 5 | 0 | 5 | 0 | 0 | 0 | 3 | 4 | 5 | 875 |
| | 2 | 4 | 1 | | 3 | 0 | 3 | 3 | 4 | 5 | 260 |
| | 3 | 4 | 1 | | 0 | 0 | 3 | 3 | 1 | 1 | 28 |
| | 4 | 4 | 1 | | 3 | 0 | 0 | 3 | 4 | 1 | 40 |
| | 5 | 5 | 0 | 5 | 3 | 0 | 0 | 3 | 4 | 5 | 1250 |
| G3 (mAb 2H8) | 1 | 4 | 5 | 0 | 3 | 0 | 3 | 3 | 4 | 1 | 260 |
| | 2 | 4 | 5 | 0 | 0 | 3 | 0 | 3 | 4 | 5 | 1000 |
| | 3 | 4 | 5 | 0 | 0 | 0 | 0 | 3 | 5 | 5 | 800 |
| | 4 | 5 | 1 | | 0 | 0 | 0 | 3 | 4 | 5 | 175 |
| | 5 | 4 | 1 | | 3 | 3 | 3 | 3 | 4 | 5 | 320 |

Figure 3:
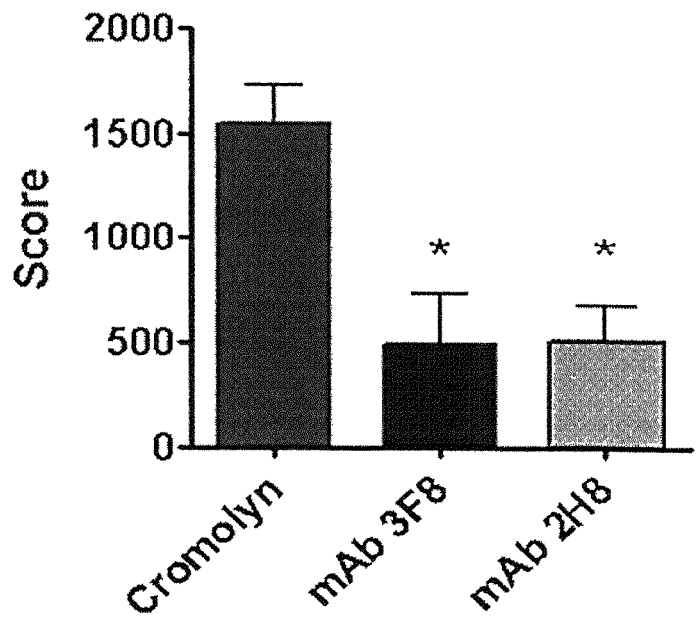
FIG. 3 shows the neutralizing effect of anti-S100P monoclonal antibodies on tumor progression and presence of liver metastases in human pancreatic BxPC3 tumors. Female, athymic, nude mice implanted with pancreatic tumors were treated daily with cromolyin (referenced blocking product of the extracellular activity of S100P) at 5 mg/Kg body weight by ip injection and antibodies against S100P (mAb 3F8 and mAb 2H8), were given three times per week at 25 mg/Kg by ip injection. Treatment groups had 5 animals. A) Effect of cromolyn and monoclonal antibodies (mAb) 3F8 and 2H8 in tumor progression analyzing the total staging endpoint score. B) Effect of cromolyn and monoclonal antibodies 3F8 and 2H8 in liver metastases calculated as photons emitted by colonizing cells per second. Graphs show the mean±standard deviation. *$p<0.05$, **$p<0.01$ ("Kruskall Wallis ANOVA nonparametric test"). The anti-S100P monoclonal antibodies from the hybridomas 3F8-1A9-2G8 (ECACC 10121604) and 2H8-3A4-2D3 (ECACC 10121603) are indicated by means of their abbreviated name 3F8 and 2H8, respectively.
Figure 3:
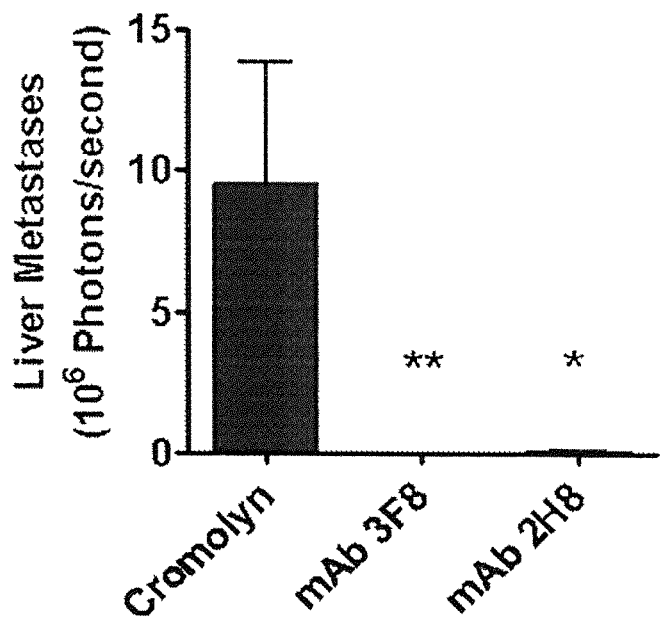

The evaluation of tumor progression (total score) shows a statistically significant decrease in animals from groups treated with either monoclonal antibody 3F8 or monoclonal antibody 2H8 compared with animals treated with the reference compound cromolyn at the best dosing schedule referenced at the bibliography (see above) for this model (FIG. 3A). In addition, these differences are reflected on the T/C ratios of total score calculated; 31%, and 32%, for 3F8 and 2H8, respectively, suggesting a significant clinical benefit for cancer therapies using monoclonal antibodies against extracellular S100P protein.

The measurements of liver metastases and calculations of photons/second emitted by the isolated organs revealed a most efficient therapeutic effectiveness in animals treated with the antibodies than animals treated with cromolyn (FIG. 3B). This best effect using the 3F8 and 2H8 monoclonal antibodies is not only observed in size of metastases but also either in number or percentage of presence of metastatic spots in treated animals.

Therefore, we demonstrate for the first time that treatment with a monoclonal antibody against S100P induced a statistically significant improved efficacy in tumor progression compared with a treatment based on Cromolyn, another product neutralizing the extracellular activity of the S100P protein in BxPC3 human pancreatic tumor and a dramatically reduction in liver metastasis.

Comparisons between groups were made using the Kruskall-Wallis ANOVA on ranks as a nonparametric test. Differences for which P value was less than 0.05 were considered statistically significant.

Example 9: Monoclonal Antibodies 2H8, 3E3 and 1A5 Block BxPC3 Tumor Growth in Nude Mice BxPC3 human pancreatic adenocarcinoma cell line in exponential growth was harvested with trypsin-EDTA (0.05%/0.02%) (Invitrogen), washed, and examined for viability by trypan blue dye exclusion. Viability was greater than 95%. For primary tumor growth, cells ($4 \times 10^6$ cells in 0.1 mL DMEM high glucose) were subcutaneously injected into the flanks of nude mice. Tumor volumes between 83-169 mm$^3$ were used to divide the mice into four groups of five mice each, such that the mean tumor size was equal between groups (approximately 120 mm$^3$). Tumor growth was followed by measuring tumor diameters with calipers and the tumor volume was calculated using an approximated formula for a prolate ellipsoid:

$$\text{volume} = (D \times d^2)/2$$

where D is the longest axis of the tumor and d the shortest. Mice were treated either with vehicle (PBS) or with the antibodies (2H8, 3E3 and 1A5), by intratumoral administration, three times per week at 100 µg/20 µL of sterile PBS, starting the treatment at defined tumor volume (120 mm$^3$), 23 days after cell implantation.

Figure 4:
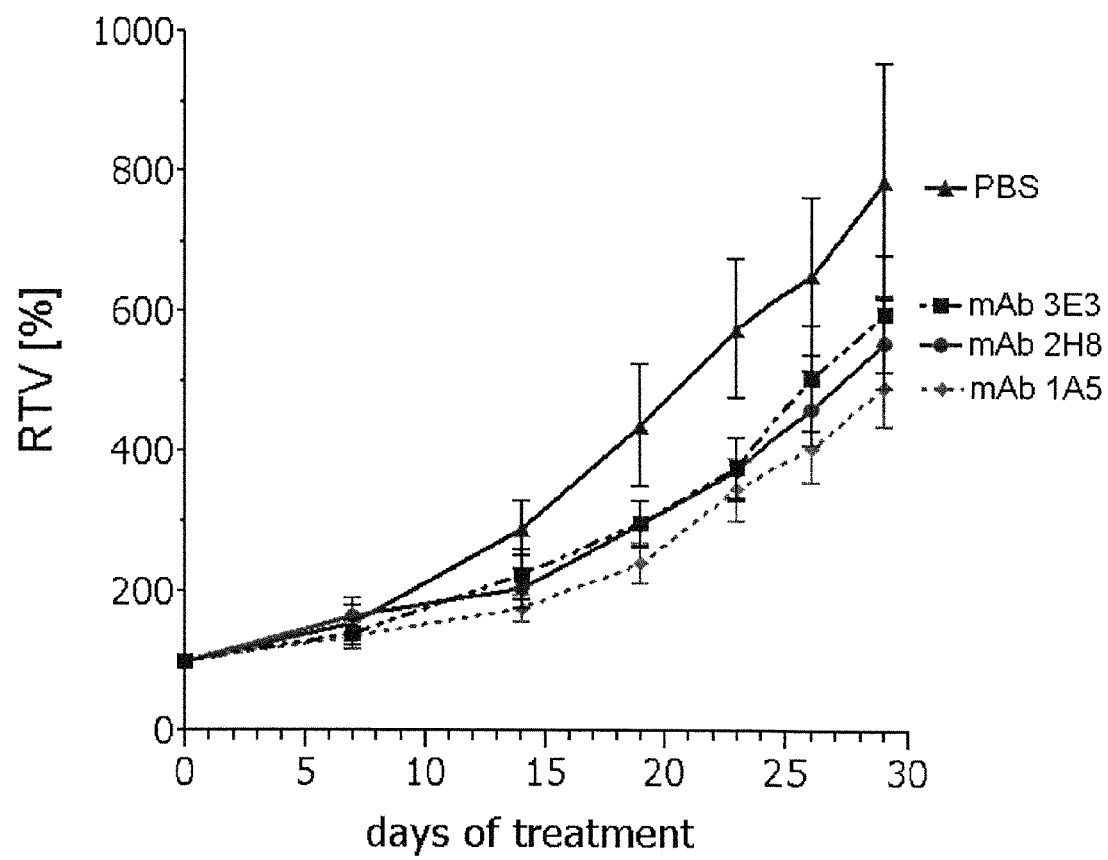
FIG. 4 shows the anti-tumor activity of monoclonal antibodies mAb 2H8, mAb 3E3 and mAb 1A5 against human S100P in human pancreatic (BxPC3) tumors. Female, athymic, nude mice were inoculated subcutaneously with $4\times10^6$ BxPC3 cells in 0.1 ml culture medium without supplements, into the right upper flank of mice on day 0. When tumors reached 83-169 mm$^3$ for BxPC3 cells, the treatment was initiated. Treatment groups had animals. PBS (negative control) and monoclonal antibody against human S100P (mAb 2H8, mAb 3E3 and mAb 1A5) at 100 µg/20 µl PBS were given by intratumoral administration three times a week. Tumor size was measured 2-3 times per week and tumor volume was calculated as described in the experimental section. Graph of relative tumor volume (RTV) shows the mean±standard deviation. The anti-S100P monoclonal antibodies from the hybridomas 3E3-2A2-5H9 (ECACC 10121602), 2H8-3A4-2D3 (ECACC 10121603) and 1A5-2G8-2D1 (ECACC 10121601) are indicated by means of their abbreviated name 3E3, 2H8 and 1A5, respectively. PBS, phosphate buffered saline.

The inventors investigated the effect of the monoclonal antibodies on the subcutaneous development of BxPC3 tumors in athymic nude mice (FIG. 4).

FIG. 4 shows the comparative analysis of the antitumoral activity of mAbs 2H8, 1A5 and 3E3 along time for BxPC3 tumor-bearing mice. Control group (vehicle, PBS) exhibited maximum tumor growth with mean relative tumor volume (RTV) of 787% respect to the initial volume (before treatment). Tumor volume changes in monoclonal antibodies-injected mice showed maximum mean relative tumor volume of 493% for 1A5, 557% for 2H8 and 598% for 3E3 at day 29 of treatment respect to the initial volume. In addition, these differences were reflected on the T/C ratios of relative tumor volume calculated; 62%, 70% and 76% for mAbs 1A5, 2H8 and 3E3 respectively compared with control group.

Therefore, we demonstrate for the first time that treatment with monoclonal antibodies against S100P induced a marked delay in tumor growth compared with control group (vehicle) for BxPC3 human pancreatic tumor.

Example 10: Plasma Determination of S100P in Xenograft Tumor Model

Blood samples from animals bearing either BxPC3 or MiaPACA-2 tumors were collected at the end of the experiment, using EDTA-coated material. Immediately after, plasma samples were centrifuged for 10 min at 5000 rpm, at room temperature and stored at −20° C. until analysis.

Plasma levels of S100P were quantified by sandwich ELISA method. Briefly, 96 microtiter plates (Maxisorb, NUNC) were coated with 10 µg/ml of monoclonal antibody 3E3 diluted in PBS (50 µl/well) 24 h at 4° C. After removing the coating, plates were washed twice with PBS and incubated 2 h at 37° C. in blocking buffer (PBS containing 2% of skimmed milk).

Plasma samples diluted 1:2 in blocking buffer were applied to the wells (50 µl/well) and were incubated 2 h at 37° C. Plates were washed five times with washing buffer (PBS-0.1% of Tween-20) and 4B12 biotinylated mouse monoclonal anti-S100P secondary antibody (Homemade) at the appropriate dilution was applied to the wells (50 µl/well) and was incubated for 1 h at 37° C.

Plates were washed five times with washing buffer and avidin/HRP (Dako) at the appropriate dilution was added to each well (50 µl/well) and were incubated 30 min at 37° C. After washing five times with washing buffer, the ELISA was revealed adding 50 µl of Tetramethylbenzidine substrate (Sigma) and were incubated 30 min at RT before stopping with 1 M of HCl. Absorbance was read at 450 nm.

Standard curve for final plasma samples (animals with tumor at the end of the experiment) was obtained by serial dilutions of human recombinant S100P in blocking buffer.

FIG. 5A shows the expression pattern of S100P protein in tumor samples derived from a MiaPACA-2 and BxPC3 cell line xenograft models. As described above regarding the corresponding cell lines, the MiaPACA-2 tumor does not express S100P while BxPC3 does. FIG. 5B shows the quantification of S100P protein in plasma samples from animals bearing MiaPACA-2 and BxPC3 subcutaneous tumors and as we can see in connection with expression in tumor samples, we were able to detect S100P levels only in plasma derived from S100P-expressing tumors.

Experimental data demonstrated the consistent statistically significant difference between null expression of S100P protein in animals with MiaPACA-2 tumors and the expression when the animals presented BxPC3 tumors.

Therefore, we demonstrate for the first time the use of a monoclonal antibody against S100P as a good tool for diagnosis of the presence of tumors expressing S100P analizing plasma and by extension any other biofluid.

Example 11: Extracellular S100P Stimulates Cell Survival and Monoclonal Antibodies 2H8, 3F8, 1A5 and 3E3 Neutralize this Effect To improve the antitumor effect and to identify new reagents for cancer treatments, we investigated the effects of the monoclonal antibodies 2H8, 3F8, 1A5 and 3E3 in combination with doxorubicin on cellular survival of HT1080 (fibrosarcoma cancer cell line) measured by MTT method.

Figure 6:
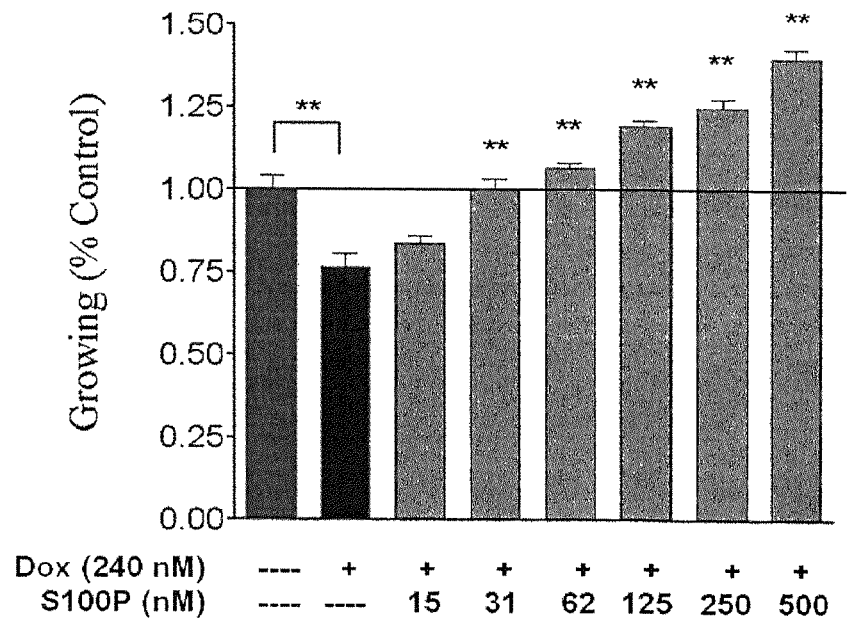
FIG. 6 shows that exogenous S100P increased cell survival of HT1080 human fibrosarcoma cell line exposed to Doxorubicin (Dox) and monoclonal antibodies (mAbs) 3F8, 2H8, 1A5 and 3E3 against S100P neutralized this effect. A) Dose dependent increase of cell survival induced by human recombinant S100P in HT1080 human fibrosarcoma cells exposed to doxorubicin (240 nM, 72 h). B) Blocking effect of monoclonal antibodies (400 nM) against S100P of cell survival promoted by S100P protein (100 nM) on cells exposed to high dose of doxorubicin (1 µM). Results are expressed as difference to corresponding controls and represent the mean±standard deviation. *$p<0.05$, **$p<0.005$ ("Mann-Whitney U test"). The anti-S100P monoclonal antibodies from the hybridomas 1A5-2G8-2D1 (ECACC 10121601), 3E3-2A2-5H9 (ECACC 10121602), 2H8-3A4-2D3 (ECACC 10121603) and 3F8-1A9-2G8 (ECACC 10121604) are indicated by means of their abbreviated name 1A5, 3E3, 2H8 and 3F8, respectively.
Figure 6:
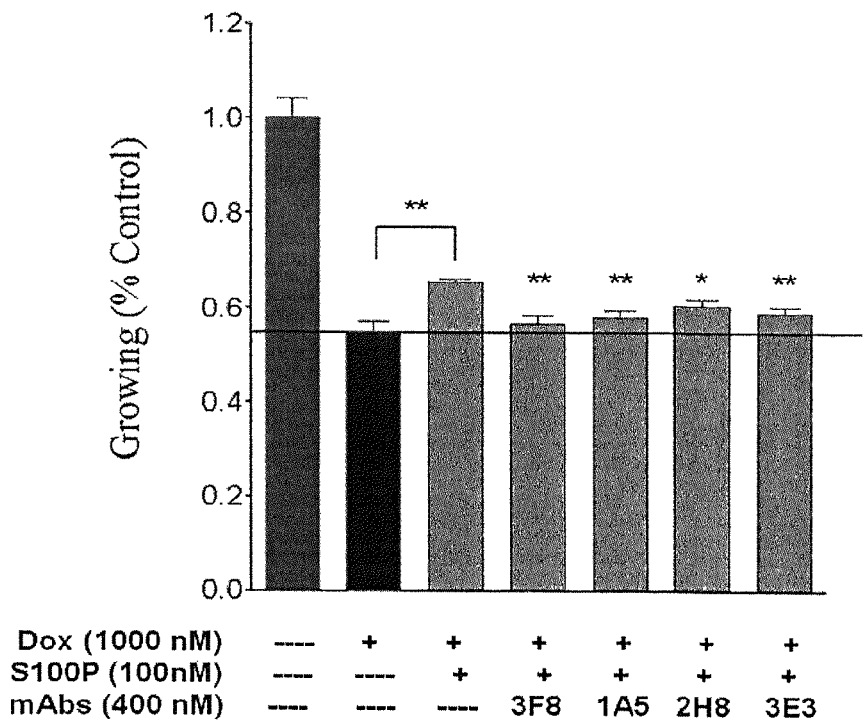

Briefly, HT1080 cells ($1 \times 10^4$ cells/well) were plated onto 96-well cell culture plates in 50 µl of DMEM medium. Twenty-for hours later, 50 µl of medium with doxorubicin (240 nM or 1 µM) alone or in combination with either S100P or S100P combined with the antibodies (see FIG. 6) were added to each well and were cultured for 72 hours. Then 10 µl of a MTT solution (5 mg/ml PBS) was added to each well and after 4 hours cells were lysed, formazan product was solubilised with 100 µl of extraction buffer (15% SDS in 50% N,N-dimethylformamide pH 4.7) and colorimetric result was measured at 570 nm using a multi-well scanning spectrophotometer 5 hours after solubilization.

Data analysis was done normalizing the results with the negative control (untreated cells) which were considered as 100% of viability.

Toxicity EC50 values chosen for doxorubicin (240 nM) were adjusted using a sigmoidal dose-response (variable slope) equation, and values were obtained from the equation:

$$Y = \text{Bottom} + (\text{Top} - \text{Bottom})/(1 + 10^{((\text{Log } EC50 - X) * \text{HillSlope})})$$

where X is the logarithm of concentration and Y is the response. Y starts at Bottom and goes to Top with a sigmoid shape.

FIG. 6A shows the extracellular role of S100P increasing the survival of HT1080 cell line, exposed to the cytotoxic agent Doxorubicin (IC50: 240 nM). The addition of S100P protected cells from injuries induced by the drug in a concentration-dependent manner with statistically significant protection from 31 nM to 500 nM of S100P. As we can see, even at 500 nM, S100P induced an increase of approximately 40% of growing respect to the non treated HT1080 cells.

FIG. 6B shows the neutralizing effect (statistically significant) of our monoclonal antibodies 2H8, 3F8, 1A5 and 3E3 (400 nM) on the protection induced by the S100P protein (100 nM) and a high dose of doxorubicin (1 μM).

This experiment demonstrated, for the first time, that the use of monoclonal antibodies against S100P decreases the cell survival induced by the protein to cells exposed to the chemotherapeutic drug doxorubicin. For this reason, monoclonal antibodies anti-S100P may prove to be novel candidates for using in combination with chemotherapeutic drugs for the treatment of patients with cancer.

Biological Material Deposits

The hybridoma which produces the 1A5-2G8-2D1 anti-S100P monoclonal antibody was deposited in the European Collection of Cell Cultures (ECACC) (Porton Down, Salisbury, SP4 OJG, United Kingdom) under the conditions stipulated in the Budapest Treaty. It was deposited on 16 Dec. 2010 and the number assigned to said deposit was 10121601.

The hybridoma which produces the 3E3-2A2-5H9 anti-S100P monoclonal antibody was deposited in the European Collection of Cell Cultures (ECACC) (Porton Down, Salisbury, SP4 OJG, United Kingdom) under the conditions stipulated in the Budapest Treaty. It was deposited on 16 Dec. 2010 and the number assigned to said deposit was 10121602.

The hybridoma which produces the 2H8-3A4-2D3 anti-S100P monoclonal antibody was deposited in the European Collection of Cell Cultures (ECACC) (Porton Down, Salisbury, SP4 OJG, United Kingdom) under the conditions stipulated in the Budapest Treaty. It was deposited on 16 Dec. 2010 and the number assigned to said deposit was 10121603.

The hybridoma which produces the 3F8-1A9-2G8 anti-S100P monoclonal antibody was deposited in the European Collection of Cell Cultures (ECACC) (Porton Down, Salisbury, SP4 OJG, United Kingdom) under the conditions stipulated in the Budapest Treaty. It was deposited on 16 Dec. 2010 and the number assigned to said deposit was 10121604.

The invention claimed is:

1. A method of treatment of cancer that expresses S100P protein, the method comprising administering to a subject in need of said treatment a pharmaceutically effective amount of a compound selected from the group consisting of:
   (i) an antibody that binds specifically to the S100P protein of SEQ ID No. 1 or of a fragment thereof with capacity for binding to the antigen; and
   (ii) a conjugate comprising a specific anti-S100P monoclonal antibody produced by a hybridoma selected from the group consisting of ECACC 10121601, ECACC 10121602, ECACC 10121603 and ECACC 10121604; or a polypeptide having at least one fragment of the sequence of said monoclonal antibody with capacity for binding to S100P protein of SEQ ID No. 1, said fragment including the sequence of the 6 CDRs of said monoclonal antibody and a second component selected from the group consisting of:
   (a) a cytotoxic agent;
   (b) an antiangiogenic agent; and
   (c) an antimetastatic agent.

2. The method according to claim 1, wherein the compound (i) is a monoclonal antibody produced by a hybridoma selected from the group consisting of ECACC 10121601, ECACC 10121602, ECACC 10121603 and ECACC 10121604 or a fragment thereof including the sequence of the 6 CDRs of said monoclonal antibody.

3. The method according to claim 1, wherein the cancer is a cancer resistant to chemotherapy treatment.

4. The method according to claim 1, wherein the cancer is selected from the group consisting of pancreatic adenocarcinoma and fibrosarcoma.

5. The method according to claim 1, wherein compound (i) is forming part of a composition comprising, together or separately, a chemotherapeutic agent.

* * * * *

SEQUENCE LISTING

```
<160> NUMBER OF SEQ ID NOS: 5

<210> SEQ ID NO 1
<211> LENGTH: 95
<212> TYPE: PRT
<213> ORGANISM: Human

<400> SEQUENCE: 1

Met Thr Glu Leu Glu Thr Ala Met Gly Met Ile Ile Asp Val Phe Ser
1               5                   10                  15

Arg Tyr Ser Gly Ser Glu Gly Ser Thr Gln Thr Leu Thr Lys Gly Glu
            20                  25                  30

Leu Lys Val Leu Met Glu Lys Glu Leu Pro Gly Phe Leu Gln Ser Gly
        35                  40                  45

Lys Asp Lys Asp Ala Val Asp Lys Leu Leu Lys Asp Leu Asp Ala Asn
    50                  55                  60

Gly Asp Ala Gln Val Asp Phe Ser Glu Phe Ile Val Phe Val Ala Ala
65                  70                  75                  80

Ile Thr Ser Ala Cys His Lys Tyr Phe Glu Lys Ala Gly Leu Lys
                85                  90                  95

<210> SEQ ID NO 2
<211> LENGTH: 98
<212> TYPE: PRT
<213> ORGANISM: Human

<400> SEQUENCE: 2

Gly Ser His Met Thr Glu Leu Glu Thr Ala Met Gly Met Ile Ile Asp
1               5                   10                  15
```

```
Val Phe Ser Arg Tyr Ser Gly Ser Glu Gly Ser Thr Gln Thr Leu Thr
            20                  25                  30

Lys Gly Glu Leu Lys Val Leu Met Glu Lys Glu Leu Pro Gly Phe Leu
        35                  40                  45

Gln Ser Gly Lys Asp Lys Asp Ala Val Asp Lys Leu Leu Lys Asp Leu
    50                  55                  60

Asp Ala Asn Gly Asp Ala Gln Val Asp Phe Ser Glu Phe Ile Val Phe
65                  70                  75                  80

Val Ala Ala Ile Thr Ser Ala Cys His Lys Tyr Phe Glu Lys Ala Gly
                85                  90                  95

Leu Lys

<210> SEQ ID NO 3
<211> LENGTH: 41
<212> TYPE: DNA
<213> ORGANISM: Artificial
<220> FEATURE:
<223> OTHER INFORMATION: S100P 5' primer

<400> SEQUENCE: 3
actcacatat gacggaacta gagacagcca tgggcatgat c                41

<210> SEQ ID NO 4
<211> LENGTH: 43
<212> TYPE: DNA
<213> ORGANISM: Artificial
<220> FEATURE:
<223> OTHER INFORMATION: S100P 3' primer

<400> SEQUENCE: 4
actcatgagc tcatcatttg agtcctgcct tctcaaagta ctt              43

<210> SEQ ID NO 5
<211> LENGTH: 6
<212> TYPE: PRT
<213> ORGANISM: Artificial Sequence
<220> FEATURE:
<223> OTHER INFORMATION: Thrombin protease cleavage site

<400> SEQUENCE: 5

Leu Val Pro Arg Gly Ser
1               5
```